(12) United States Patent
Khanifar et al.

(10) Patent No.: US 12,028,957 B1
(45) Date of Patent: Jul. 2, 2024

(54) RADIO FREQUENCY FLUID WARMER AND METHOD

(71) Applicant: LINAMP TECHNOLOGIES LLC, Laguna Hills, CA (US)

(72) Inventors: Ahmad Khanifar, Laguna Hills, CA (US); Elham Khanifar, Laguna Hills, CA (US)

(73) Assignee: LINAMP TECHNOLOGIES LLC, Laguna Hills, CA (US)

( * ) Notice: Subject to any disclaimer, the term of this patent is extended or adjusted under 35 U.S.C. 154(b) by 649 days.

(21) Appl. No.: 17/202,097

(22) Filed: Mar. 15, 2021

Related U.S. Application Data

(63) Continuation-in-part of application No. 15/918,981, filed on Mar. 12, 2018, now Pat. No. 10,952,290, which is a continuation of application No. 15/454,051, filed on Mar. 9, 2017, now Pat. No. 9,949,321.

(60) Provisional application No. 62/305,998, filed on Mar. 9, 2016.

(51) Int. Cl.
| | |
|---|---|
| *H05B 6/80* | (2006.01) |
| *A61M 1/28* | (2006.01) |
| *A61M 5/44* | (2006.01) |
| *H05B 6/70* | (2006.01) |

(52) U.S. Cl.
CPC .............. *H05B 6/802* (2013.01); *A61M 1/282* (2014.02); *A61M 1/284* (2014.02); *A61M 5/445* (2013.01); *H05B 6/705* (2013.01); *A61M 2205/3368* (2013.01); *A61M 2205/368* (2013.01)

(58) Field of Classification Search
CPC ........ H05B 6/802; H05B 6/705; A61M 1/282; A61M 1/284; A61M 5/445; A61M 2205/3368; A61M 2205/368
USPC ....... 219/628, 629, 630, 678, 679, 687–696, 219/702, 704, 710–713, 761, 762; 604/27, 48, 14, 113, 114; 607/90, 607/98–106; 606/27–31
See application file for complete search history.

(56) References Cited

U.S. PATENT DOCUMENTS

| | | | |
|---|---|---|---|
| 4,207,452 A | 6/1980 | Arai | |
| 4,417,116 A * | 11/1983 | Black | H05B 6/804 219/688 |
| 5,073,167 A | 12/1991 | Carr et al. | |
| 5,683,381 A | 11/1997 | Carr et al. | |
| 5,690,614 A | 11/1997 | Carr et al. | |
| 5,895,548 A | 4/1999 | Ettinger | |

(Continued)

*Primary Examiner* — Quang T Van
(74) *Attorney, Agent, or Firm* — Jafari Law Group, Inc.

(57) ABSTRACT

The present invention is generally a radio frequency apparatus for warming fluids such as IV fluids. In exemplary embodiments, a uniform warming of fluids is achieved by exposing a fluid-carrying tube to Radio Frequency (RF) energy. The RF energy may be supplied by an RF generator, which is coupled to a waveguide. The waveguide typically includes an inlet into which a fluid tube may be introduced. Inside the waveguide, a pathway may be formed wherein the fluid tube may rest in a predetermined position. In exemplary embodiments, the pathway guides the positioning of the tube along a transmission-line length of the waveguide, in a manner such that the tube gradually approaches an electromagnetic field inside the waveguide and exits at a second terminal end of the waveguide. Having absorbed energy supplied from the RF generator, the fluid inside the tube exits the apparatus warmed to a desired temperature.

10 Claims, 15 Drawing Sheets

(56) References Cited

U.S. PATENT DOCUMENTS

| | | |
|---|---|---|
| 5,919,218 A | 7/1999 | Carr |
| 6,146,359 A | 11/2000 | Carr et al. |
| 2008/0277389 A1 | 11/2008 | Carr |

* cited by examiner

RADIO FREQUENCY FLUID WARMER AND METHOD

PRIORITY NOTICE

The present application is a Continuation-in-Part Application of U.S. patent application Ser. No. 15/918,981 filed Mar. 12, 2018, which is a Continuation of U.S. patent application Ser. No. 15/454,051 filed Mar. 9, 2017, which claims priority under 35 U.S.C. § 119(e) to U.S. Provisional Patent Application Ser. No. 62/305,998 filed on Mar. 9, 2016, the disclosures of which are incorporated herein by reference in their entirety.

COPYRIGHT & TRADEMARK NOTICE

A portion of the disclosure of this patent application may contain material that is subject to copyright protection. The owner has no objection to the facsimile reproduction by any one of the patent documents or the patent disclosures, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and shall not be construed as descriptive or to limit the scope of this invention to material associated only with such marks.

TECHNICAL FIELD OF THE INVENTION

The present invention relates in general to a system and method for warming fluids using radio frequency, and more specifically, to a radio frequency fluid warmer and method that may be utilized to warm therapeutic fluids.

BACKGROUND OF THE INVENTION

Warming of fluids has various applications in any number of fields, for example medicine. In the medical field, warming of fluids is desirable during various procedures, particularly in those involving the intravenous administration of fluids to a patient. This issue becomes important given that certain fluids vital to patient resuscitation (such as blood or blood products) require preservation and storage at low temperatures in order to prevent them from spoiling or contamination. Hence administration of such fluids (e.g. packed red blood cells) requires warming them in order to avoid causing hypothermia in the patient receiving it. Other fluids may require warming prior to being intravenously infused in a patient even though said fluids may be stored at room temperature. It is important to note that the human body's normal temperature, which is critical to normal physiologic homeostasis (typically around 37 degrees Celsius), may be significantly higher than room temperature. Therefore, exposure of patients (intravenous or any other route) to therapeutic fluids that are lower than normal body temperature may not only cause significant discomfort, but also have physiologic consequences which can cause adverse clinical effects and unwanted outcomes. Accordingly, several systems, apparatus, and methods are found in the prior art describing different means to warm fluids such as refrigerated blood and other fluids that require intravenous or intraperitoneal administration. Unfortunately, the prior art solutions are riddled with numerous problems that have yet to be properly addressed.

One common problem is the application of non-uniform electric fields to warm a therapeutic fluid such as intravenous (IV) fluid, which result in an inhomogeneous heating of the liquids. Other problems are presented by conduction heating methods, such as methods that pass blood through heated conduits, which are energy inefficient, less portable and slow, and thus impractical in emergency situations. Other more advanced methods include the introduction of microwave heating, but these methods too have been shown to introduce their own challenges. Primarily, it is now well known that simply heating fluids such as blood (i.e. for example by placing a blood bag inside a conventional microwave oven) carries unacceptable risks given that heating blood in this manner does not result in a uniform distribution of heat throughout the fluid being heated. This important issue is a result of the manner in which microwaves are introduced that leads to generation of hotspots, exposing some areas of the fluid being warmed to excess heat. This will not only be undesirable given the non-uniform nature of heating, but can also lead to adverse effects such as damage to components of the fluid being warmed (i.e. damage to red blood cells or protein structure/function).

While some current methods appear to address hotspots created by systems that implement microwave heating means, these systems appear to rely on components and apparatuses that themselves present additional problems; such problems include introduction of additional steps/equipment (cartridges) in the fluid delivery apparatus (i.e. tubing). This disrupts the continuity of the delivery system (by requiring the tubing to be connected to a cartridge) and creates points where error and contamination can occur, hence raising safety and sterilization concerns. The following examples merely illustrate some of the problems found in the prior art.

One application requiring the warming of such fluids prior to administration includes the warming of peritoneal dialysis dialysate prior to intraperitoneal infusion. For example, certain patients with end-stage renal disease require renal replacement therapy for survival. One modality of renal replacement therapy is peritoneal dialysis (PD); a PD catheter is placed in the patients' abdomen and dialysates (either sterile solutions containing fixed amounts of electrolytes, lactate and dextrose or other infusate such as Icodextrin) are infused into the peritoneal cavity. During treatment, the patient's peritoneal membrane is used as a dialysis membrane and excess serum electrolytes and toxins are removed via diffusion into the dialysate. Given the large volume of dialysates needed each time a patient fills their peritoneal cavity (on average between 2.0-2.5 L), this fluid is usually warmed to between 35° C. and 37° C. to avoid patient discomfort and other unwanted side effects of hypothermia given cool fluid is entering the abdomen. The current system used to warm PD dialysates relies on heat conduction. The warming process is highly inefficient and is fraught with excess time and energy wastage. The system requires warming up a large surface of the dialysis machine and relies on conduction of this heat to a PD dialysate bag, which is placed on top of this surface.

While there are reports of patients/dialysis centers using microwave ovens to warm PD dialysate fluid, this practice is not sanctioned by the US Food and Drug Administration (FDA) or manufacturers of PD solutions, given the potential for formation of hot spots during use of conventional microwave ovens. This is in light of the fact that there are several reported studies in the literature noting mere exposure to RF energy is safe and efficient, and does not lead to disturbance of the PD dialysate content or the integrity of the bag. Several publications provide discussion of these issues such as "Control of microwave heating of peritoneal dialysis solutions" by Deutschendorf A F, Wenk R E, Lustgarten J, Mason P., appearing in Peritoneal dialysis international: journal of the International Society for Peritoneal Dialysis. 1994; 14(2): 163-7; "Microwave ovens for heating fluid bags for continuous ambulatory peritoneal dialysis" by Hudson S, Stewart W K, appearing in British medical journal. 1985; 290(6486):1989; "Rapid warming of infusion solution" by Yamada Y, Yasoshima A. appearing in Surgery, Gynecology & Obstetrics. 1985; 160(5): 400-2; and "Microwave warming of peritoneal dialysis fluid" by Armstrong S, Zalatan S J. appearing in ANNA journal/American Nephrology Nurses' Association. 1992; 19(6): 535-9; discussion 40. However, regardless of these reports, significant safety concerns surrounding hotspot generation and non-uniform warming of dialysate, which can result in serious complications, have precluded routine use of general microwave ovens as a means of warming peritoneal dialysate.

Another important area where warming of therapeutic fluids is of significant value is in critical care when either large volume resuscitation is needed (i.e. liver transplantation, trauma from motor vehicle accidents or battlefield injuries) or in the peri-intra-postoperative period. In many cases the latter scenarios are interrelated and in all cases patients can suffer clinically significant hypothermia. Hypothermia, defined as core temperature <36° C. during a procedure, is a common problem in critical care and among surgical patients. In the case of patients undergoing surgery, an incidence of 4% to 72%, and up to 90% has been reported. Intraoperative hypothermia has been associated with significant clinical complications, including risk of cardiovascular adverse effects, issues with hemostasis and perioperative hemorrhage, increased risk of postoperative infection and disturbed drug metabolism. Given these significant complications, many professional societies, such as the Association of periOperative Registered Nurses (AORN), www.aorn.org, and the National Institute for Health and Care Excellence (NICE), www.nice.nhs.uk, have recommendations in place for preventing and treating during the perioperative period. While there are many factors which may contribute to hypothermia the use of un-warmed fluids for intravenous infusion has been deemed to play a major role. While the positive effects of normothermia in these patients has been documented, the role of warming of patients or infused fluids has been mainly studied using incubators and convection methods. "The effects of warming intravenous fluids on intraoperative hypothermia and postoperative shivering during prolonged abdominal surgery" by Camus Y, Delva E, Cohen S, Lienhart A published in Acta Anaesthesiol Scand. 1996 August; 40(7):779-82. "The effects of intravenous fluids temperature on perioperative hemodynamic situation, post-operative shivering, and recovery in orthopaedic surgery" by Hasankhani H, Mohammadi E, Moazzami F, Mokhtari M, Naghgizadh M M. published in the journal Can Oper Room Nurs J. 2007 March; 25(1):20-4, 26-7. Again, these methods are fraught with inefficiency, lack of portability and excess time requirement. Therefore, novel fluid warming technologies which can address hypothermia in the scenarios mentioned will be of significant value. The application of microwave technology has been limited and will be discussed in the next section.

Another important application involves the need for warming of blood and blood products (red blood cell transfusion); a treatment which becomes necessary to maintain the oxygen-carrying capacity in patients with severe anemia, especially those who have suffered major trauma or patients undergoing major surgery. During resuscitation of the latter patients, multiple units of blood products or packed red blood cells (PRBCs) may be administered in a short period of time. Such products or PRBC units are normally refrigerated at low temperatures of 4±2° C. prior to transfusion. The FDA regulation recommends storage temperature in the range of 1° C.-6° C.; "Safe storage" would be considered to be void if the temperature exceeds 8° C. (See for example FDA "Guide to inspections of blood banks," published by the FDA, Office of Regulatory Affairs Washington. 14 Sep. 1994).

For patients requiring large volumes of blood transfusion, to prevent hypothermia, the PRBCs units must be warmed up rapidly and almost immediately before transfusion. Aside from the inherent energy inefficiency of convection heating methods, using known means that implement conduction, could prove problematic; especially in emergency situations where considerable transfusions are required to be infused rapidly.

Although delays resulting from heating means relying on conduction of heat appeared to have been addressed by microwave heating methods, these systems proved similarly problematic. The use of conventional microwave ovens or other adapted derivatives to warm blood and IV products became popular soon after the introduction of commercial microwave ovens in the mid-1950s and was regularly used up until the 1970s. Such devices offer shorter heating times than the convectional heaters such as those using a water bath, but several reports of complications from overheating of blood products led to abandonment of microwave oven blood warmers. See for example "Danger of overwarming blood by microwave" by Arens J F, Leonard G L published in Jama. 1971; 218(7): 1045-6. Considerable ongoing debates remain regarding the use of these devices (see for example, "Indicators of erythrocyte damage after microwave warming of packed red blood cells" by Hirsch J, Menzebach A, Welters I D, Dietrich G V, Katz N, Hempelmann G. published in Clinical chemistry. 2003; 49(5): 792-9; and "Temperature course and distribution during plasma heating with a microwave device" by Hirsch J, Bach R, Menzebach A, Welters I D, Dietrich G V, Hempelmann G. published in Anesthesia 2003; 58(5): 444-7).

There are several reports that describe the use of various microwave-based techniques to warm blood products, which do not involve heating up a blood bag inside a microwave oven, per se. However, each of these methods is complicated by an apparent inability to avoid hot spots, or use techniques that require the use of a disposable cartridge. The former having the potential to damage or inadequately heat up the fluids; the latter introducing a point of disruption in the delivery of the infusate which can create the potential for clinically significant adverse events such as entry of air, contaminants or infection given that the need for a cartridge breaks the continuous sterile transfusion system (i.e. the tubing connecting the infusate to the patient). In addition, the need for a cartridge adds another layer of cost and complexity which is less desirable. (See for example, "Microwave applications in clinical medicine" by Lantis J C, 2nd, Carr K L, Grabowy R, Connolly R J, Schwaitzberg S D. published in Surgical endoscopy. 1998; 12(2): 170-6; "The limits of bloodwarming: maximally heating blood with an inline microwave blood warmer" by Herron D M, Grabowy R, Connolly R, Schwaitzberg S D. published in The Journal of trauma, 1997; 43(2): 219-26; discussion 26-8; "In-line microwave blood warming of in-date human packed red blood cells" by Pappas C G, Paddock H, Goyette P, Grabowy R, Connolly R J, Schwaitzberg S D. published in Critical care medicine, 1995; 23(7): 1243-50; "The effect of in-line microwave energy on blood: a potential modality for blood warming" by Holzman S, Connolly R J, Schwaitzberg S D. published in The Journal of trauma. 1992; 33(1):89-93; discussion-4; and "Rapid in-line blood warming using microwave energy: preliminary studies." By Schwaitzberg S D, Allen M J, Connolly R J, Grabowy R S, Can K L, Cleveland R J. published in Journal of investigative surgery: the official journal of the Academy of Surgical Research. 1991; 4(4):505-10).

Accordingly, there is an unanticipated and significant clinical need, which is inadequately addressed at this time for warming fluids. More specifically, there is a need in the art for a fluid warming technique whereby fluids, such as intravenous (IV) fluids, can be warmed to the desired temperature via a warmer apparatus that avoids the potential complications of localized overheating, or exposure to hotspots altogether. Furthermore, there is a need for a fluid warming technique and apparatus that is more portable and does away with cartridges or components that break a closed sterilized system, minimizing risk of error or infection and avoiding safety and sterilization challenges presented by current means.

Therefore, there is a need in the art for a radio frequency fluid warmer and method that may be utilized to warm fluids, including IV fluids, which adequately addresses the problems with the prior art. It is to these ends that the present invention has been developed.

BRIEF SUMMARY OF THE INVENTION

To minimize the limitations in the prior art, and to minimize other limitations that will be apparent upon reading and understanding the present specification, the present invention describes a radio frequency fluid warmer and method that may be utilized to warm therapeutic fluids.

A radio frequency fluid warmer apparatus, in accordance with an exemplary embodiment of the present invention, comprises: a waveguide including first and second electromagnetic ports, an inlet for receiving a fluid, and an outlet for dispensing the fluid; a tube for routing the fluid inside the waveguide between the inlet and the outlet during operation of the apparatus; a source of electromagnetic energy coupled to the first electromagnetic port; and a termination coupled to the second electromagnetic port for preserving a matched waveguide condition.

A radio frequency fluid warmer apparatus, in accordance with another exemplary embodiment of the present invention, comprises: a waveguide including first and second electromagnetic ports, an inlet, and an outlet for receiving a fluid tube that traverses the waveguide; a pathway situated inside the waveguide for routing the fluid tube between the inlet and the outlet; a radio frequency generator coupled to the first electromagnetic port; and a termination coupled to the second electromagnetic port for preserving a matched waveguide condition.

A system for warming intravenous fluids using radio frequency signals, in accordance with an exemplary embodiment of the present invention, comprises: a rectangular waveguide including first and second electromagnetic ports, an inlet situated substantially at a sidewall of the rectangular waveguide for receiving a fluid, and an outlet for dispensing the fluid; a control module configured to: generate radio frequency signals from an energy source; and apply the radio frequency signals to the first electromagnetic port; a tube for routing the fluid inside the rectangular waveguide between the inlet and the outlet during operation of the system; and a termination coupled to the second electromagnetic port for preserving a matched waveguide condition.

A radio frequency fluid warmer system, in accordance with the present invention, may include: a waveguide including first and second electromagnetic ports, an inlet, and an outlet for receiving a fluid-carrying tube that traverses the waveguide; a radio frequency generator coupled to the first electromagnetic port; a resistive termination coupled to the second electromagnetic port for preserving a matched waveguide condition; and a control module in communication with one or more sensors situated in proximity to the inlet and outlet of the waveguide, the control module configured to: monitor a temperature of the fluid inside the fluid-carrying tube based on sensing data of the one or more sensors; and control a power level of the radio frequency generator in response to the sensing data.

A method performed by radio frequency fluid warmer system, in accordance with the present invention, may include the steps of: controlling a power level of a radio frequency generator coupled to a first electromagnetic port of a waveguide, wherein the waveguide includes a resistive termination coupled to a second electromagnetic port of the waveguide for preserving a matched waveguide condition, and wherein the waveguide is adapted to receive a fluid-carrying tube positioned between an inlet and an outlet of the waveguide; receiving sensing data from one or more sensors situated in proximity to the inlet or the outlet of the waveguide; and monitoring a parameter of a fluid inside the fluid-carrying tube based on sensing data from the one or more sensors.

It is an objective of the present invention to provide an RF frequency fluid warming device that avoids hot-spots.

It is another objective of the present invention to uniformly warm fluids.

It is yet another objective of the present invention to provide a fluid warming device which does not require any additional supplemental equipment (such as a cartridge) and does not disrupt the continuity of the fluid deliver system.

It is yet another objective of the present invention to provide a compact, energy efficient, transportable fluid warming device.

These and other advantages and features of the present invention are described herein with specificity so as to make the present invention understandable to one of ordinary skill in the art.

BRIEF DESCRIPTION OF DRAWINGS

Elements and embodiments in the figures have not necessarily been drawn to scale in order to enhance their clarity and improve understanding of the invention. Furthermore, elements that are known to be common and well understood to those in the industry are not depicted in order to provide a clear view of the various embodiments of the invention.

DETAILED DESCRIPTION OF THE INVENTION

Figure 1:
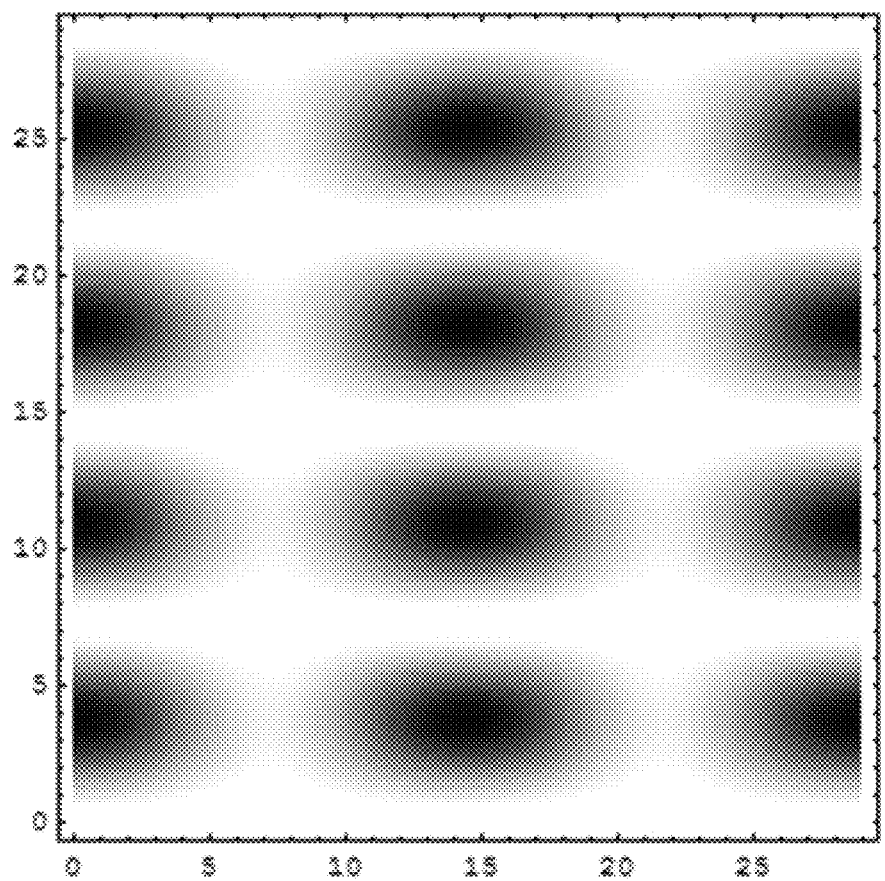
FIG. 1 depicts a formation of hot-spots, which may be found in a typical microwave cavity (such as the inside of a microwave oven), illustrating a common problem of using microwaves to heat certain types of fluids.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of example in order to provide a thorough understanding of the relevant teachings. However, it should be apparent to those skilled in the art that the present teachings may be practiced without such details. In other instances, well known structures, components and/or functional or structural relationships thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and or steps are in any way required for one or more embodiments, whether these features, elements and/or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

Generally, the present invention involves an in-line real-time radio frequency apparatus for warming fluids, including but not limited to IV fluids. In exemplary embodiments, an in-line heating or warming of fluids may be achieved by means of exposing a fluid having an initial temperature to Radio Frequency (RF) energy. The RF energy may be supplied by an appropriately configured, digitally controlled, RF generator that generates the RF energy into a containment vessel or waveguide. The waveguide typically includes a first terminal end including a point of entry into which a fluid tube may be introduced, and a second terminal end from which the fluid tube may exit the waveguide. Inside the waveguide, a pathway may be formed wherein the fluid tube may rest in a predetermined position. In exemplary embodiments, the pathway guides the positioning of the tube along a transmission-line length of the waveguide, in a manner such that the tube gradually approaches an electromagnetic field inside the waveguide and exits at the second terminal end of the waveguide. The fluid inside the tube, having been gradually exposed to the RF energy inside the waveguide, may absorb energy at a substantially constant rate per unit length, and exit the waveguide at a temperature higher than the fluid's initial temperature. The apparatus is typically non-invasive and may be constructed using a suitable high-frequency transmission-line structure such as a rectangular, circular or elliptical waveguide operating in an appropriate mode of propagation. In exemplary embodiments, the in-line exposure to RF energy is substantially along the transmission-line length, and in a manner, which prevents unsafe over-exposure and overheating of the fluid as it traverses through the warming apparatus, by for example, implementing a gradual and predefined coupling rate of RF energy to the fluid-carrying tube along the transmission-line length. In exemplary embodiments, a non-invasive temperature monitoring subsystem may be employed for monitoring the temperature of the liquid flowing in the tube. Automatic fail-safe controls may comprise of an "operator watch" safety-check to prevent operator errors. Moreover, inlet and outlet temperatures may be continuously sampled to monitor and control the power level of applied RF energy to the waveguide, in order to achieve the desired temperature while avoiding over or under heating.

In the present specification, the term fluid may refer to, but is not limited to, IV fluids, dialysates, blood or blood products, replacement fluids for continuous renal replacement therapy (CRRT), dialysis water, or any other fluid or therapeutic fluid that may be administered to a patient. For example, and without limiting the scope of the present invention, fluids in this disclosure may refer to various concentrations of saline, lactated ringer, D5W, blood products (including but not limited to packed red blood cells, fresh frozen plasma, platelets and cryoprecipitate), peritoneal dialysis dialysate, hemodialysis dialysate/water, continuous renal replacement therapy replacement fluid and dialysates, plasmapheresis and plasma exchange blood products prior to use in patients, or any other fluids including fluids that may require warming prior to or concurrent with medical procedures. Of course, a person of ordinary skill in the art will appreciate that other fluids, including fluids that may not necessarily have therapeutic properties, may be warmed or heated using an apparatus in accordance with the present invention.

An apparatus in accordance with present invention is entirely different from the methodologies previously disclosed in the prior art and avoids the shortcomings of the previous systems. To illustrate the problems addressed by a system in accordance with the present invention, a brief detailed examination of microwave technology explains the causes for concerns with application of devices or any adapted derivatives that employ RF energy as a means to warm fluids, particularly IV fluids. To such ends, and now turning the first figure, FIG. 1 depicts a formation of hot-spots, which may be found in a typical microwave cavity (such as the inside of a microwave oven), illustrating a common problem of using microwaves to heat certain types of fluids.

More specifically, FIG. 1 shows the energy distribution in a microwave cavity or resonator is not uniform, and the temperature of the target (for example a fluid-containing bag) at hotspots (i.e. the dark spots) can easily exceed safe limits. Based on the below analysis, the application of any cavity-based microwave ovens regardless of configuration should be considered as potentially unsafe. This analogy can be extended to any enclosed cavity system that may be used to warm or heat certain fluids, including IV fluids.

A microwave oven in its simplest form comprises of a continuous wave (CW) or pulsed RF source at the 2.45 GHz range. In microwave ovens, the RF source is normally a magnetron which is a high-power high-frequency tube oscillator. Recently, solid state sources are becoming available for such applications. The RF generator is coupled to the microwave cavity or warming cavity. A short section of metallic waveguide connects the RF generator to the warming cavity. The applied RF energy excites a cavity mode in the warming cavity. The formation of a cavity mode is due to propagation of electromagnetic waves between the walls of the enclosed cavity leading to the formation of a standing wave pattern with peaks (nodes) and troughs (antinode), wherein the nodes are hot-spots such as those seen in FIG. 1.

The following explains the causes of hot spot formation inside a microwave cavity. The RF electric field component inside the cavity may be given as follows:

$$E_x = E_1 \cos(k_x x)\sin(k_y y)\sin(k_z z)e^{i\omega t}, \quad (1);$$

$$E_y = E_2 \sin(k_x x)\cos(k_y y)\sin(k_z z)e^{i\omega t}, \quad (2); \text{ and}$$

$$E_z = E_3 \sin(k_x x)\sin(k_y y)\cos(k_z z)e^{i\omega t}, \quad (3),$$

where $\omega$ is the angular frequency of the microwave, and $k_x$, $k_y$ and $k_z$ are given by:

$$k_x = \frac{m\pi}{L_x}, k_y = \frac{n\pi}{L_y}, k_z = \frac{p\pi}{L_z} \text{ and } m, n, p = 0, 1, 2, \ldots, \quad (4)$$

where $L_x$, $L_y$ and $L_z$ are dimensions of the cooking cavity, and $E_1$, $E_2$ and $E_3$ are constrained by:

$$k_x E_1 + k_y E_2 + k_z E_3 = 0, \quad (5), \text{ and}$$

the average power density absorbed by a load in the microwave (e.g. food) may be given as:

$$\langle P \rangle \propto \langle E^2 \rangle, \quad (6)$$

$$\text{where } \langle E^2 \rangle = \frac{1}{2}(|E_x|^2 + |E_y|^2 + |E_z|^2), \quad (7)$$

Given suitable values of m, n and q which are a function of cavity size, a typical power distribution may be as shown in FIG. 1. Thus, this shows that an RF cavity structure that generates a standing-wave pattern for RF heating inside an enclosed warming cavity will have hot-spots. Standing-waves are generated when the energy travels in two opposing directions, which occurs when the RF energy is bounced back and forth by reflective (metallic) cavity walls. Therefore, to achieve uniform heating inside a waveguide, the formation of standing waves must be avoided.

Accordingly, the present invention provides for uniform RF heating by implementing a system that instead generates a travelling wave when applying RF energy to the system's waveguide. As will be discussed in turn with reference to the remaining figures, by facilitating the formation of a travelling wave heating structure including a waveguide that is appropriately matched at its terminals, the present invention enables an efficient, quick heating means of warming fluids in a uniform and homologous manner.

Figure 2A:
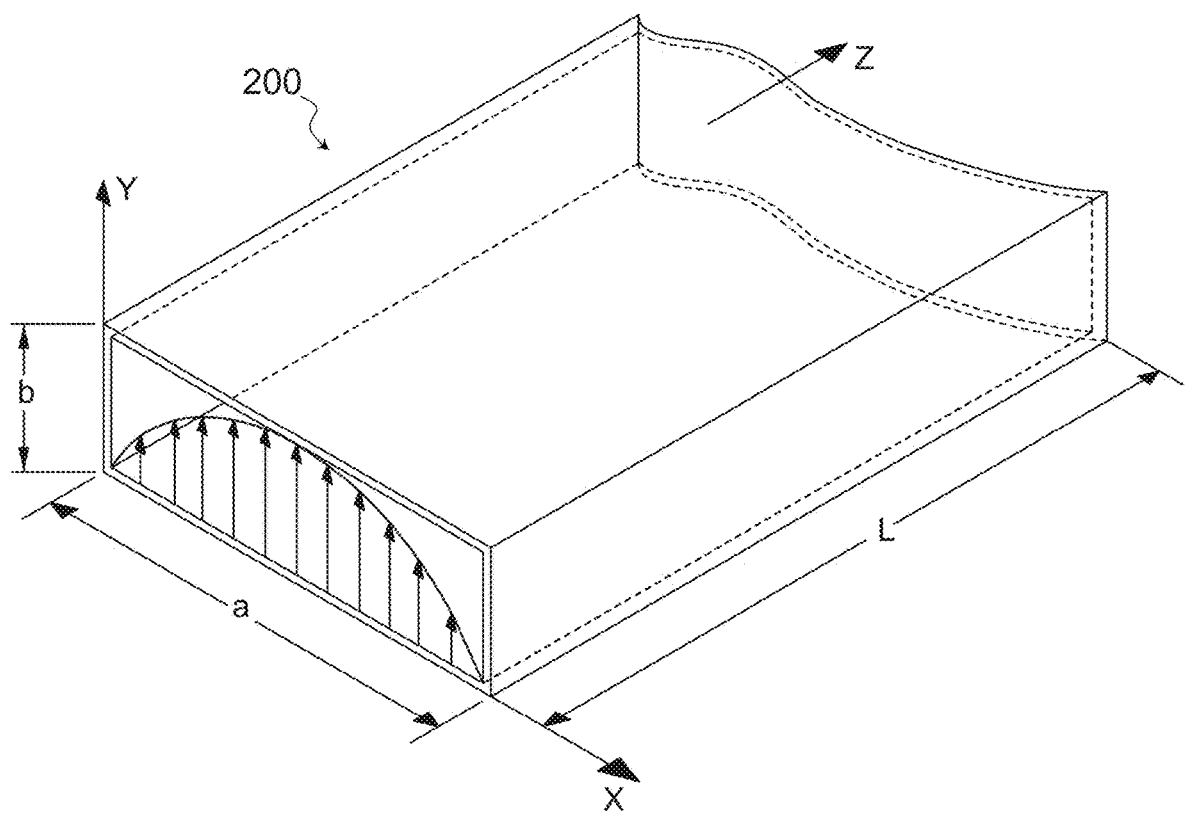
FIG. 2(a) and FIG. 2(b) illustrate an exemplary rectangular waveguide field pattern in accordance with practice of the present invention.
Figure 2B:
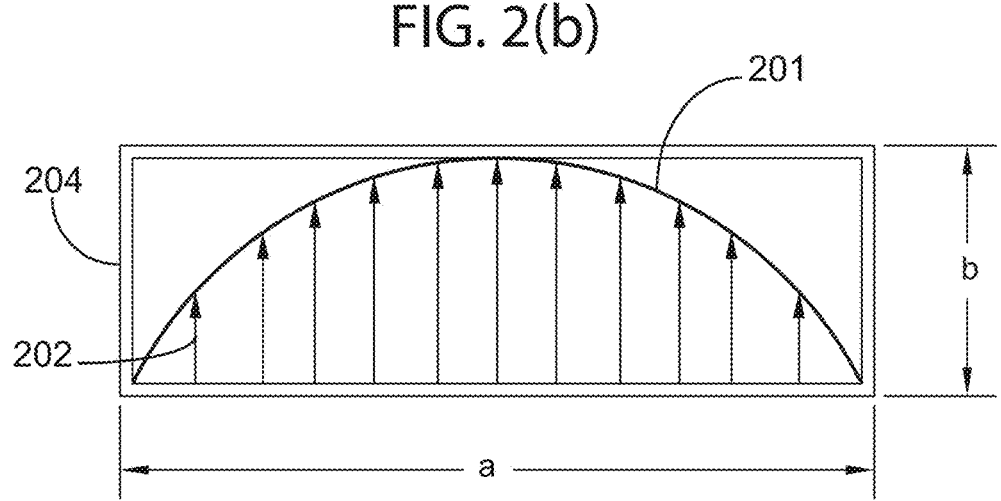

Turning now to the figures depicting the invention, FIG. 2(a) and FIG. 2(b) illustrate an exemplary rectangular waveguide field pattern in accordance with practice of the present invention. More specifically, FIG. 2(a) and FIG. 2(b) illustrate a diagram that helps explain the coupling of energy from a waveguide 200 to a fluid-carrying tube (not shown in this figure), utilizing a specific property of electric field pattern generated inside waveguide 200.

As mentioned above, waveguide 200 in accordance with an exemplary embodiment of the present invention may include any number of structural designs, and may comprise of a rectangular waveguide as shown having a length L, a width a, and a height b; however, this particular geometry is not a limiting case and other geometries with similar field patterns are equally appropriate, including circular or elliptical cross-sections, and variations such as ridged waveguides and others would not deviate from the scope of the present invention.

Waveguide 200 is shown as a substantially rectangular structure, in accordance with an exemplary embodiment of the present invention, having an electric field generated perpendicular (along height b) to the direction of propagation (along length L) through waveguide 200; as shown, the dominant transverse electric (TE) mode waveguide 200 is in $TE_{10}$. In this mode of excitation, the peak of envelope 201 of electric field 202 is half sine in shape, i.e. the field intensity is maximum at the center of waveguide 200's broad dimension (width a) and its intensity decreases to zero approaching each of the waveguide side walls 204. Accordingly, in order to tap the maximum energy from waveguide 200, a fluid-carrying tube may be placed at the center of waveguide 200, meaning positioning the tube at substantially half a and along length L of waveguide 200. Conversely, to minimize the energy absorption of a fluid introduced into waveguide 200, a fluid-carrying tube may be placed closer to the side walls 204. Consequently, as shown in FIG. 2(a) and FIG. 2(b), the location of the fluid-carrying tube (e.g. an IV tube) in waveguide 200 will determine the amount of energy absorption by the fluid-carrying tube.

It should be noted that while the current disclosure focuses on a rectangular waveguide propagation in $TE_{10}$ mode of operation, other geometries and supporting modes may be utilized without deviating from the scope of the present invention.

For example, the envelope of the field intensity across the cross section of a rectangular waveguide can be calculated analytically or simulated using numerical techniques. Such techniques are well known to those skilled in the art. As depicted by the plot of electric field pattern illustrated in FIG. 2, the electric field envelop peaks across the waveguide's cross section; showing a half sinusoidal variation across the broad dimension of waveguide 200. If a waveguide is excited at its $TE_{20}$ mode, a similar analysis will show a full sinusoidal variation and the electric filed will peak twice across the waveguide opening. Accordingly, both $TE_{10}$ and $TE_{20}$ can be utilized for the intended application. As an example, however, and in no way intended to limit the scope of the present disclosure, this specification focuses on the $TE_{10}$ mode as an illustrative embodiment.

As such, in an exemplary embodiment of the present invention, the available RF energy peaks at the center of the broad dimension or width a (as shown in FIGS. 2(a) and 2(b)) and the intensity reduces near the sidewalls. Therefore, if a fluid carrying tube is placed along the length L of waveguide 200 (i.e. within a pathway, for example), the RF energy will interact with the fluid in the tube and the energy absorption rate will be a function of location of the tube within the waveguide's cross-section, so that, with reference to FIGS. 2(a) and 2(b) for example, the absorbed energy is a function of x (or a width along the length of the waveguide). The following figure illustrates such embodiment.

Figure 3:
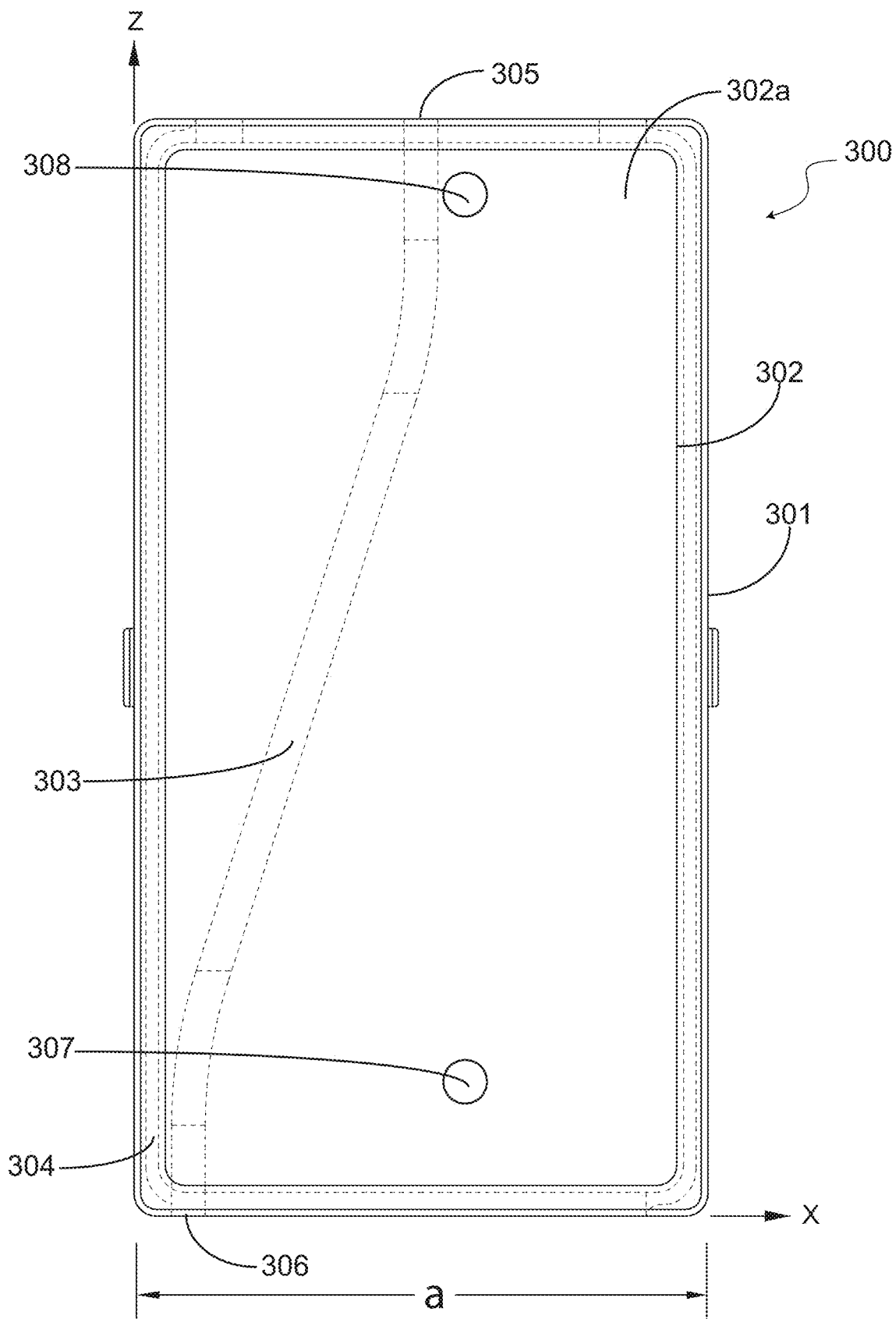
FIG. 3 illustrates a top cross-sectional view of a rectangular waveguide showing an exemplary pathway in which a fluid tube may be positioned, in accordance with an exemplary embodiment of the present invention.

Turning now to the next figure, FIG. 3 illustrates a top view of a rectangular waveguide showing an exemplary cavity, conduit, or pathway in which a fluid tube may be positioned, in accordance with an exemplary embodiment of the present invention. More specifically, waveguide 300 is shown comprising a housing or clam shell, which includes a first shell 301 and a second shell 302, that may be decoupled from each other so that one of the shells acts as a top shell that encloses or envelops portions of a base shell.

In exemplary embodiments, as will be discussed further below with reference to other figures, the top shell is substantially hollow and the base shell (for example, second shell 302) may be filled with a foam structure 302a that is lightweight but allows for the formation of a cavity, conduit or pathway 303 in which to position a fluid tube, such as an IV fluid tube. In the embodiment shown, depicted in a cross-sectional top view, it can be appreciated that the insertion of a tube positioned within pathway 303, which runs along the length or the z-axes of waveguide 300, will alter the hallow waveguide structure in terms of RF energy conduction. As mentioned above, the location of a fluid-carrying tube along pathway 303 will determine the amount of energy absorption or heat generated in the fluid-carrying tube.

In exemplary embodiments, waveguide 300 is a partial dielectric-filled waveguide. As a person of ordinary skill in the art will appreciate, power loss (and conversion to heat) in a waveguide transmission-line is caused by imperfection of wall conductors and the dielectric filling the waveguide. Therefore, input RF power may be gradually attenuated as the input RF signal travels along the guide between RF input port 307 and terminated port 308. The attenuation factor for a transmission-line in may be defined as:

$$\alpha = \frac{\text{Power lost in unit length}}{2 \times \text{power transmitted}}, \quad (8)$$

where: $\alpha=\alpha_c+\alpha_d$; $\alpha_c$=the attenuation factor due to the walls' ohmic resistance; and $\alpha_d$=the dielectric loss per unit length.

Figure 9:
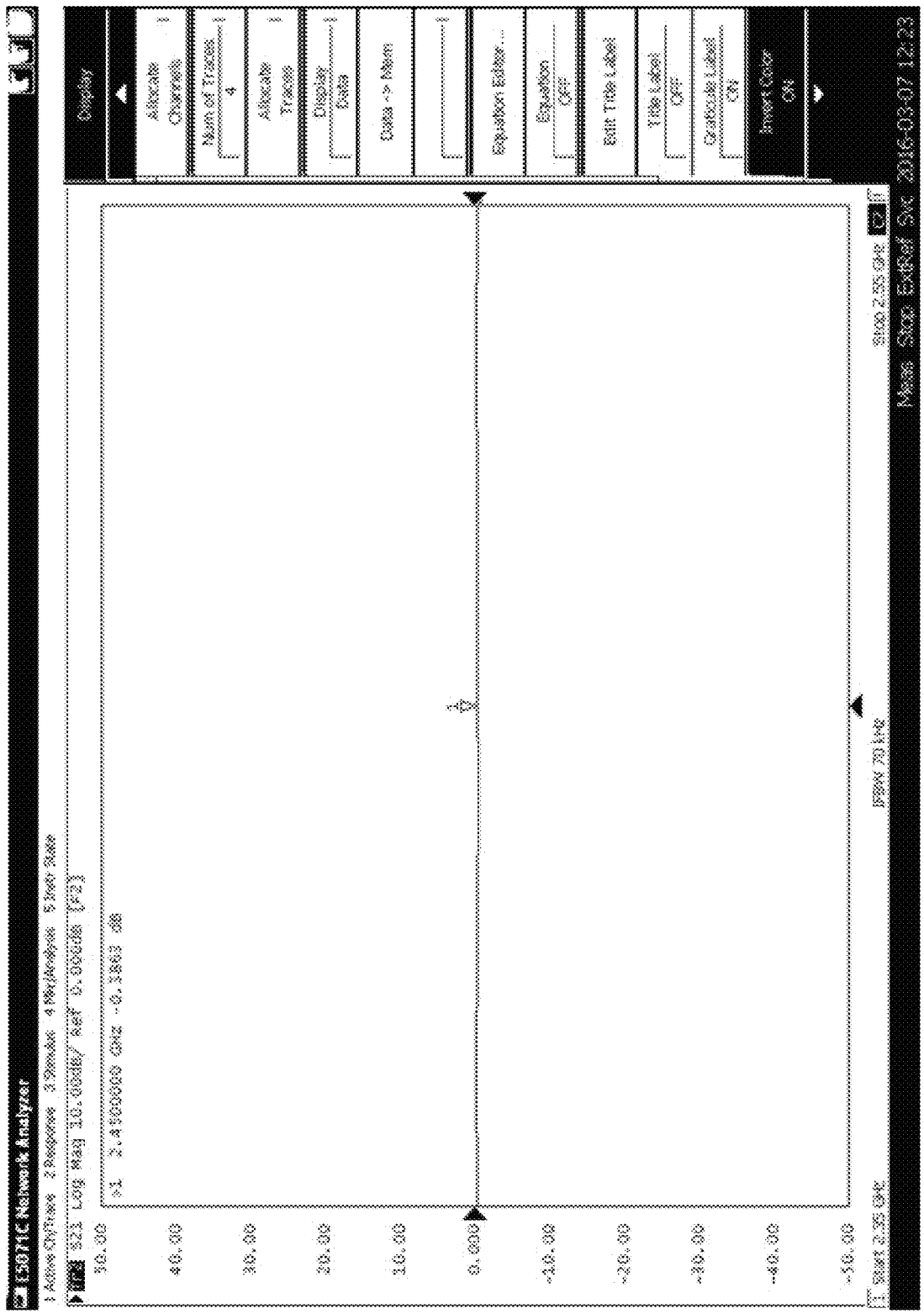
FIG. 9 illustrates a screenshot of an analysis tool showing infusion tube losses, without liquid.
Figure 10:
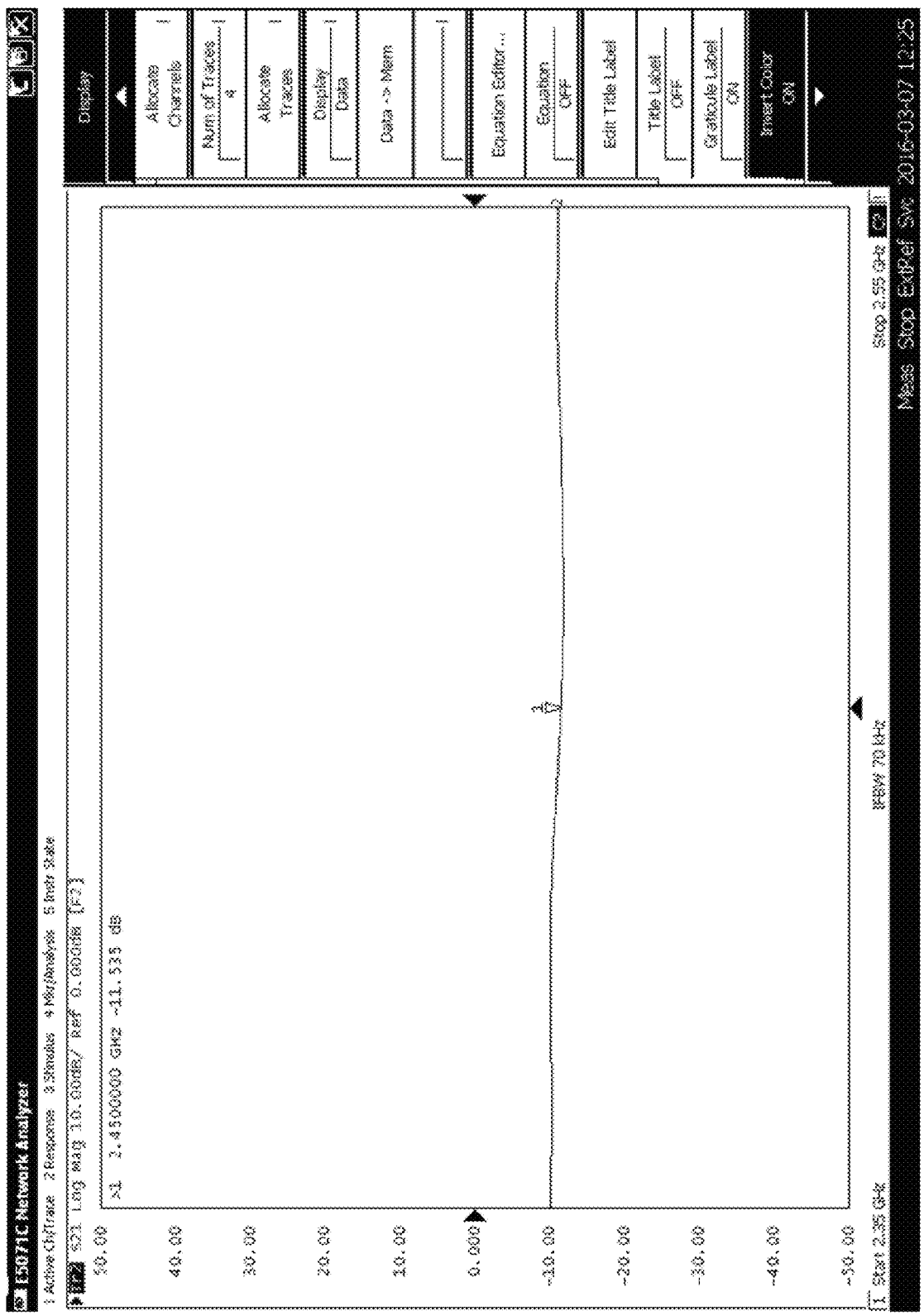
FIG. 10 illustrates a screenshot of an analysis tool showing infusion tube losses, with liquid.

In an air-filled waveguide (i.e. without a tube inserted), the $\alpha_c >> \alpha_d$. However, when the fluid-carrying tube is inserted in the waveguide, the waveguide gets loaded and the dielectric loss will dominate, i.e., $\alpha_c << \alpha_d$ in which case the fluid (i.e. inside the fluid-carrying tube) absorbs the RF energy and heats up. This is shown in FIG. 9-FIG. 10.

The signal attenuation caused by fluid absorption may be calculated from:

$$\text{insertion loss}=10\log e^{2\alpha l} \quad (9),$$

where $\alpha$ is the combined loss-coefficients and is dominated by $\alpha_d$. The $\alpha_d$ is the attenuation factor of loss caused by the tube and the fluid. FIG. 9 shows that the tube loss (with no fluid) is negligibly small whereas the flow of fluid in the tube constitutes the dominant share of loss ($\alpha_d$) as shown in FIG. 10, which is caused by absorption of RF energy and heating the fluid in the tube.

Accordingly, it is noted that the insertion loss of a fluid-carrying tube, or a loaded waveguide, is proportional to the length l where the fluid-carrying tube interacts with the electric field in the waveguide. As discussed earlier, the RF heating would be maximum if the tube is always located at the center of the guide, and the heating rate (i.e. heat generated per unit length) will be highest closer to the RF source or RF input port 307, and lowest closer to the terminated port 308, which is situated at a low intensity RF section of waveguide 300.

However, a fluid warming apparatus in accordance with the present invention preferably, especially for applications involving certain medical fluids, includes a pathway positioned such as pathway 303, which gradually veers away from side-walls 304 towards a center portion of waveguide 300.

In such embodiment, for $TE_{10}$ mode, the attenuation factor $\alpha_d$ will be modified by $$\sin^2\left(\frac{m\pi x}{a}\right)$$

term (where for $TE_{10}$, m=1 and n=0). Here "x" (see FIG. 2, FIG. 3) is the variable that defines the tube location across length L of the waveguide. For example, for x=0 at (waveguide wall, or for example waveguide inlet opening 306) the dielectric attenuation (attenuation factor $\alpha_d$) is reduced to zero and no heat is generated assuming dominant a d as discussed above. The attenuation (absorption) will be maximum at $$x=\frac{a}{2}$$

(i.e., at the center of the front wall of the waveguide that includes the inlet).

The following Table 1.0 discloses an exemplary means for a uniform distribution of heat along the length of waveguide 300. Of course, this is shown by way of example and in no way is Table 1.0 intended to limit the scope of the present invention. Assuming a typical waveguide construction for waveguide 300, wherein a fluid-carrying tube has been positioned along pathway 303, and wherein L is 20 cm, the absorption rate in each increment of $\Delta l=1$ cm may exemplarily follow the Table 1.0 below, in order to achieve a uniform heat generation.

TABLE 1.0

| Tube length increments | Input power level at each increment | Power absorbed in each increment | Power absorbed dB |
|---|---|---|---|
| 1 | 100 | 0.05 | −13.01029996 |
| 2 | 95 | 0.052631579 | −12.78753601 |
| 3 | 90 | 0.055555556 | −12.55272505 |
| 4 | 85 | 0.058823529 | −12.30448921 |
| 5 | 80 | 0.0625 | −12.04119983 |
| 6 | 75 | 0.066666667 | −11.76091259 |
| 7 | 70 | 0.071428571 | −11.46128036 |
| 8 | 65 | 0.076923077 | −11.13943352 |
| 9 | 60 | 0.083333333 | −10.79181246 |
| 10 | 55 | 0.090909091 | −10.41392685 |
| 11 | 50 | 0.1 | −10 |
| 12 | 45 | 0.111111111 | −9.542425094 |
| 13 | 40 | 0.125 | −9.03089987 |
| 14 | 35 | 0.142857143 | −8.4509804 |
| 15 | 30 | 0.166666667 | −7.781512504 |
| 16 | 25 | 0.2 | −6.989700043 |
| 17 | 20 | 0.25 | −6.020599913 |
| 18 | 15 | 0.333333333 | −4.771212547 |
| 19 | 10 | 0.5 | −3.010299957 |
| 20 | 5 | 1 | 3.85731E−15 |

Figure 8:
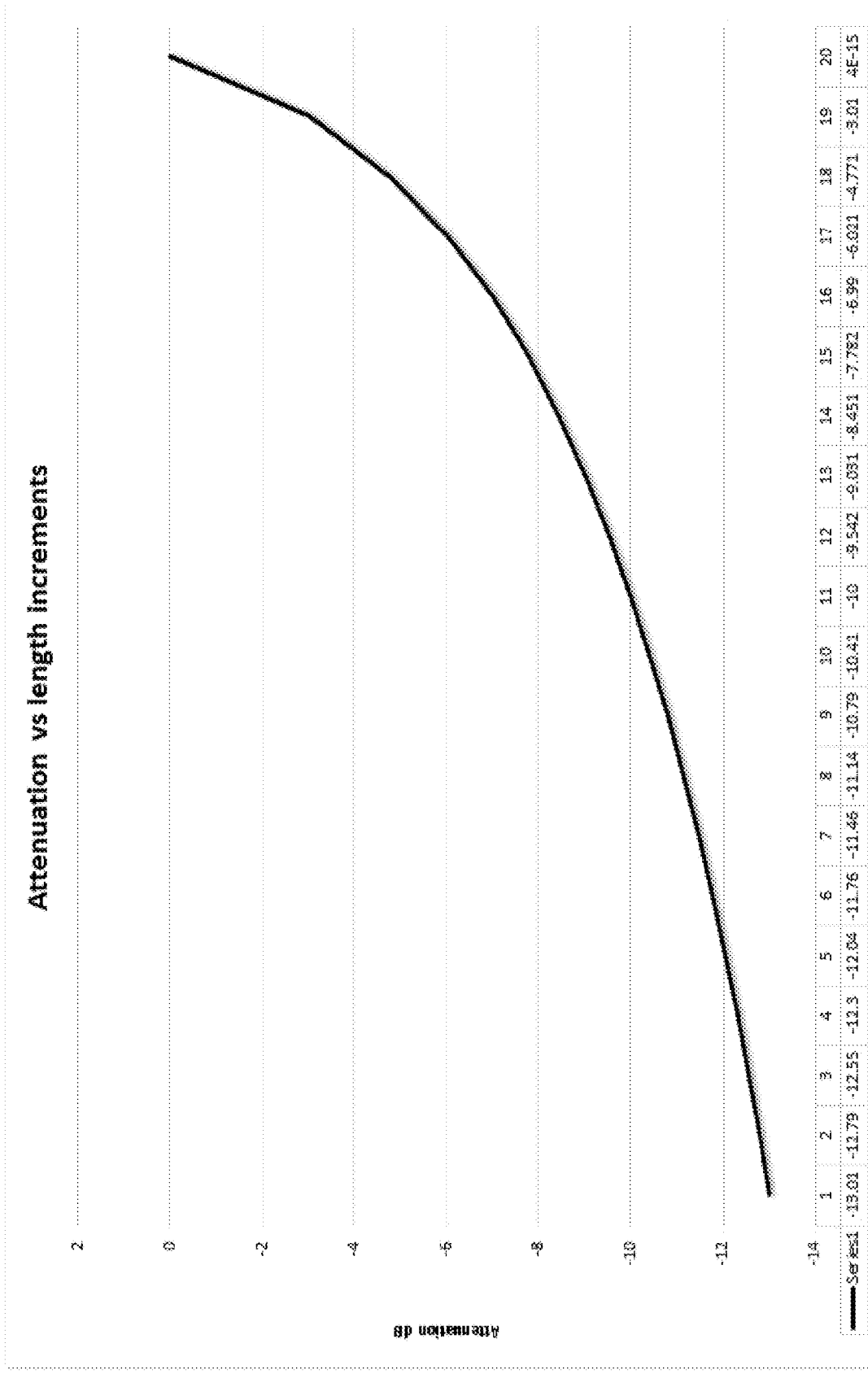
FIG. 8 is a graph showing attenuation versus length increments, which illustrates absorption rate along the length of an intravenous fluid-carrying tube.

More specifically, Table 1.0 above shows the RF energy absorption rate along the length of waveguide for uniform heat generation; this may be plotted as shown in FIG. 8. Referring to equation (7), the RF energy is given as:

$$P \propto \langle E^2 \rangle = \frac{1}{2\mu_{TE}}E_y^2 = \frac{1}{2\mu_{TE}}E_0^2\sin^2\left(\frac{\pi x}{a}\right), \quad (10)$$

where "a" is the broad dimension of waveguide 300 and "x" is the location of the fluid-carrying tube across the waveguide's length L, and power "P" is constant per unit length along the waveguide length L.

Figure 4:
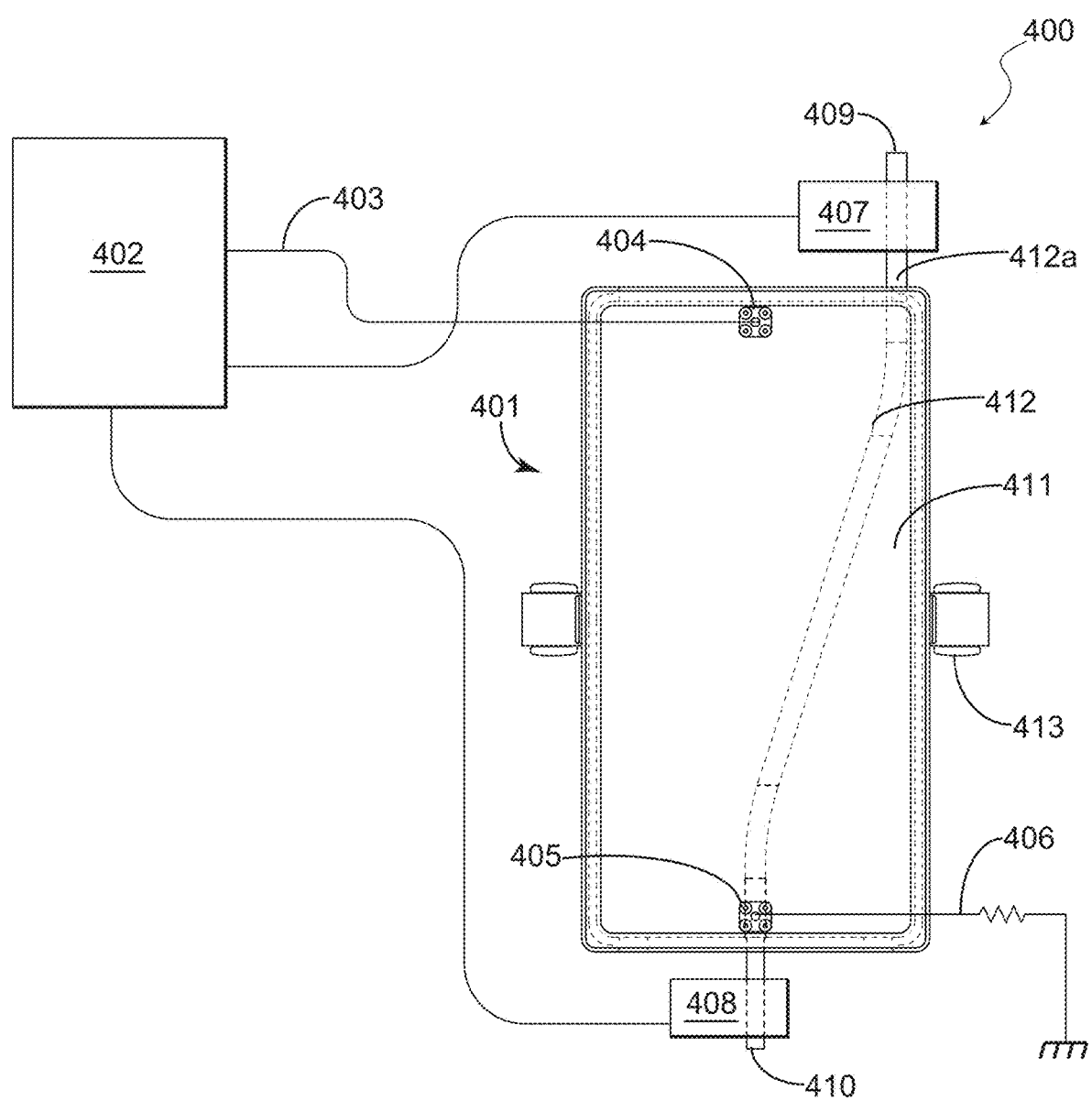
FIG. 4 illustrates a system for warming fluids in accordance with an exemplary embodiment of the present invention.

Turning now to the next figure, FIG. 4 illustrates a system for warming fluids in accordance with an exemplary embodiment of the present invention. More specifically, FIG. 4 depicts an RF fluid warmer system (system 400), which comprises: waveguide 401; an RF source control module (control module 402); an RF input line 403 that introduces RF signals into waveguide 401 via a first electromagnetic port or RF input port 404; a termination comprising terminal port 405 connected to an RF connector 406, which collects any unabsorbed portion of the input power and dumps it in a matched load; and temperature sensors 407 and 408 situated at input terminal end 409 and output terminal end 410, respectively, for non-invasively measuring (and enabling temperature monitoring and control via control module 402) the temperature of the fluid entering and exiting waveguide 401. As in previous figures, waveguide 401 is also shown from a top cross-sectional view in which the interior portion of the containment vessel or waveguide 401 can be appreciated. As shown, waveguide 401 typically includes a structure such as foam structure 411, which includes a pathway 412 (similar to pathway 303 in FIG. 3, for example) that facilitates the positioning, or guides, fluid-carrying tube 412*a*. Furthermore, waveguide 401 includes two clamps 413 that hold the two halves of the containment vessel or housing of waveguide 401 together after the insertion of the tube and while the apparatus is operational.

The exemplary embodiment depicted in FIG. 4 insures the waveguide (RF transmission line) of system 400 remains properly terminated at all times, albeit with or without fluid running in the tube; the termination eliminating the formation of hotspots inside the waveguide because the termination preserves the matched waveguide condition. As indicated above, RF connector 406 is attached to the surface of waveguide 401 at port 405, which is situated at a terminal end of waveguide 401. The termination, or RF connector 406 that is connected to a monopole radiator inside the waveguide via the second electromagnetic port or termination port 405, is matched to waveguide impedance. The mono pole probe acts as a waveguide-to-coaxial-line transformer. The output of this transformer is connected to a matched load (for example, an RF 5052 load) capable of absorbing the RF energy flowing in waveguide 401. Such energy could be an excess power not absorbed by infusion fluid or even in the absence of a fluid flow. This component effectively eliminates an otherwise reflection of energy back to control module 402 and prevents the formation of a standing wave pattern (i.e. "hot-spots") within waveguide 401, as discussed above. The matched load is normally attached to the waveguide surface, which will act as a heatsink. In practice, the heat sinking requirement is short lived and is only expected when the RF is "ON" but no fluid is flowing through the tube. Moreover, in exemplary embodiments, in the event that fluid fails to flow in the fluid tube, control module 402 may shut off the RF source after a programmable time, in accordance with one or more sets of executable instructions stored or accessible to control module 402.

It is noted here that according to foregoing embodiments of this disclosure, by properly positioning a fluid-carrying tube inside the length (along for example the Z-axis as shown in FIG. 3) of a waveguide, there should be minimal left-over RF energy at the end of the waveguide length, i.e., the tube outlet. Accordingly, the tube outlet can be positioned in the middle section of the waveguide terminal wall (see for example outlet opening 305 depicted in FIG. 3) so that the tube exits from a middle portion of the waveguide. Alternatively, and without limiting the scope of the present invention in any way, a practical alternative may be to position the tube outlet closer to the side-walls so as to eliminate interference with the monopole probe extending into the waveguide from the terminal port. Naturally, other similar alternatives based on design constraints, such as any other convenient location for an outlet opening, may be implemented without deviating from the scope of the present invention. This is more clearly illustrated in a block diagram presented in the following referenced figure.

Figure 7:
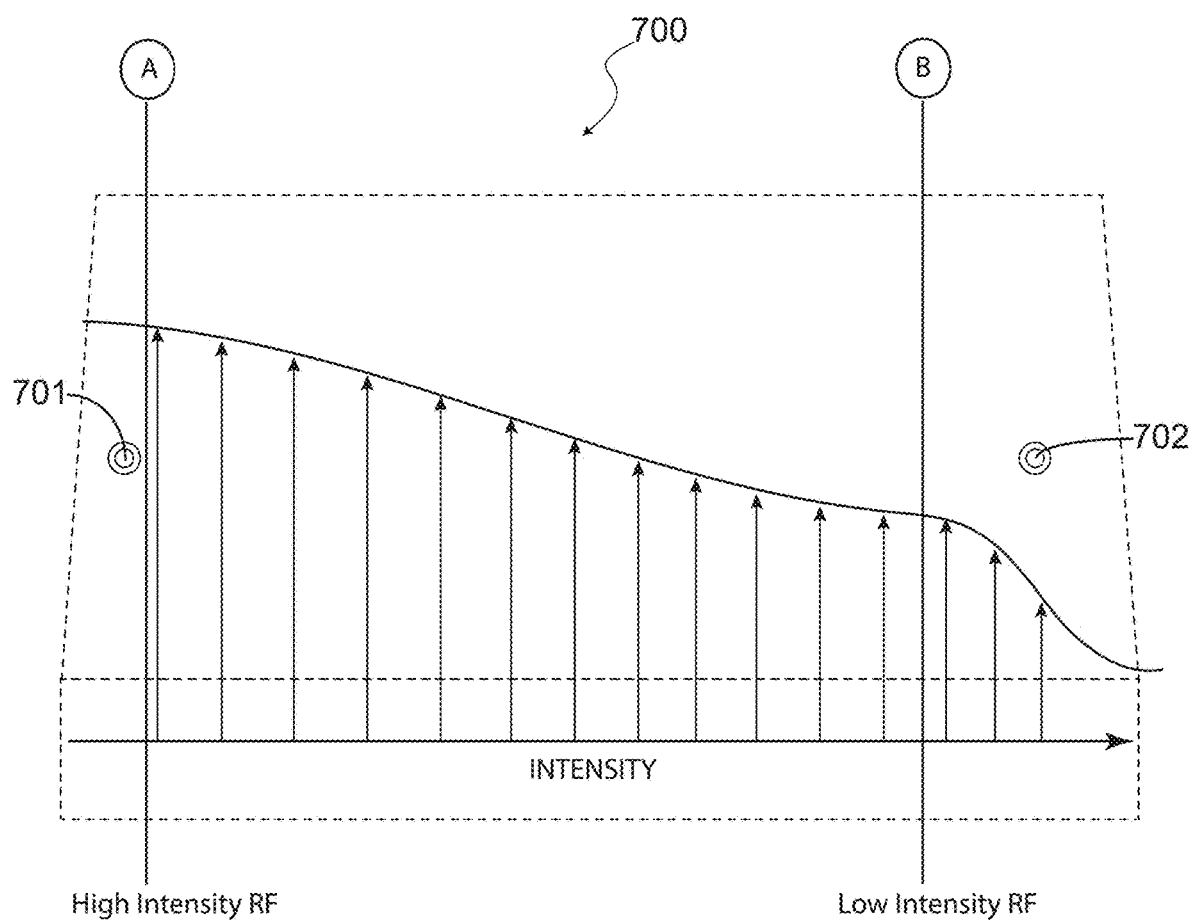
FIG. 7 is a diagram showing an exemplary pathway of a fluid-carrying tube inside a waveguide with corresponding energy intensity therethrough, in accordance with an exemplary embodiment of the present invention.

FIG. 7 is a diagram showing an exemplary pathway of a fluid-carrying tube inside a waveguide with corresponding energy intensity therethrough, in accordance with an exemplary embodiment of the present invention. From this diagram, it may be appreciated that in waveguide 700 including RF input port 701 and RF terminal port 702, the intensity decreases from segment A near the RF input port where RF signals are introduced into waveguide 700, to segment B near RF terminal port 702 where an RF connector collects any unabsorbed portion of the input power and dumps it in a matched load (i.e. termination). As mentioned above, because there may be some structural design considerations that are facilitated by alternative placements of an outlet for a fluid carrying-tube, different positions may be selected for such outlet since as shown in the FIG. 7, after a certain segment B along the length of waveguide 700, the RF intensity is low and will not significantly affect the fluid inside the tube so far as the position out of which the tube exits the waveguide. As mentioned above, however, it can be appreciated from FIG. 7 that an inlet or input portion of a pathway traversing the waveguide is preferably substantially at a sidewall of the waveguide, since the intensity at or near segment A is high and thus could, for example, damage certain fluids.

The above embodiments provide an important and useful advantage of having a terminated waveguide warmer, wherein no priming is required during the startup phase of the fluid warmer. A start-up process in accordance with practice of exemplary embodiments of the present invention may be as follows: Turn on RF generator (the RF termination absorbs the unused RF energy); Turn on the fluid, (where the fluid in the tube will absorb the RF energy and very little will be absorbed by the terminating load); Allow trapped air to exit; and Start the infusion. It is pointed out that this process does not require priming the fluid warmer during which cold fluid has to be collected and disposed.

Figure 5A:
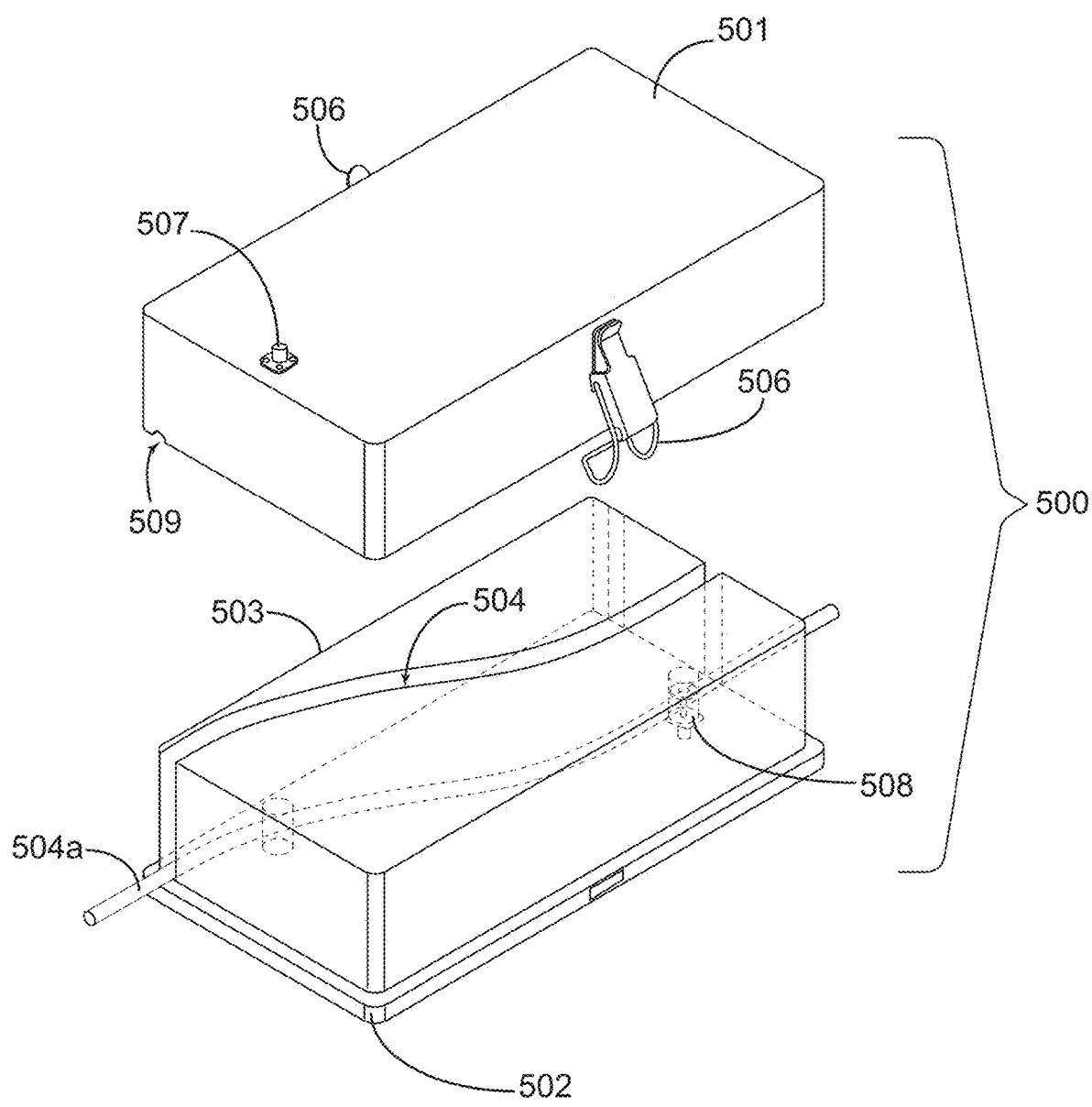
FIG. 5(a) illustrates a fluid warming apparatus for a system for warming fluids in accordance with an exemplary embodiment of the present invention.
Figure 5B:
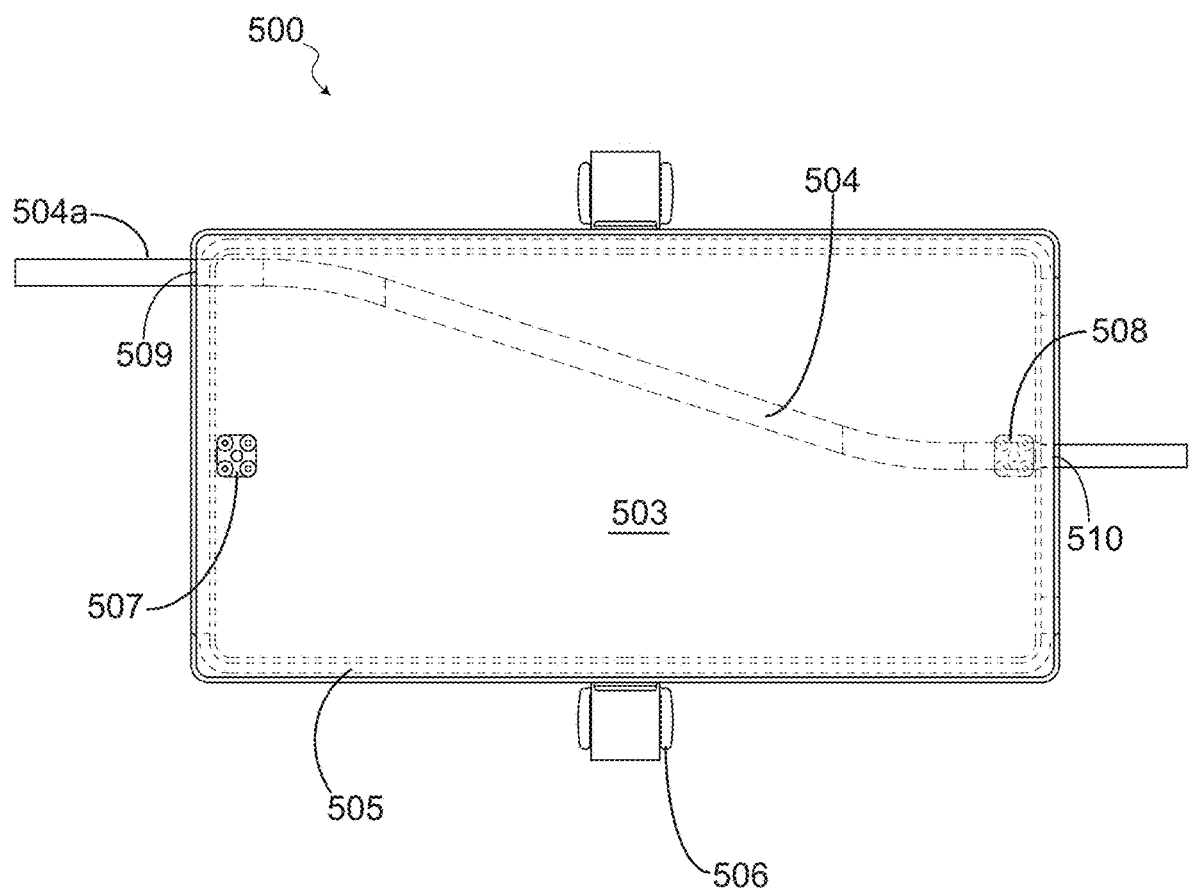
FIG. 5(b) illustrates a cross-sectional top view of the apparatus illustrated in FIG. 5(a).
Figure 6A:
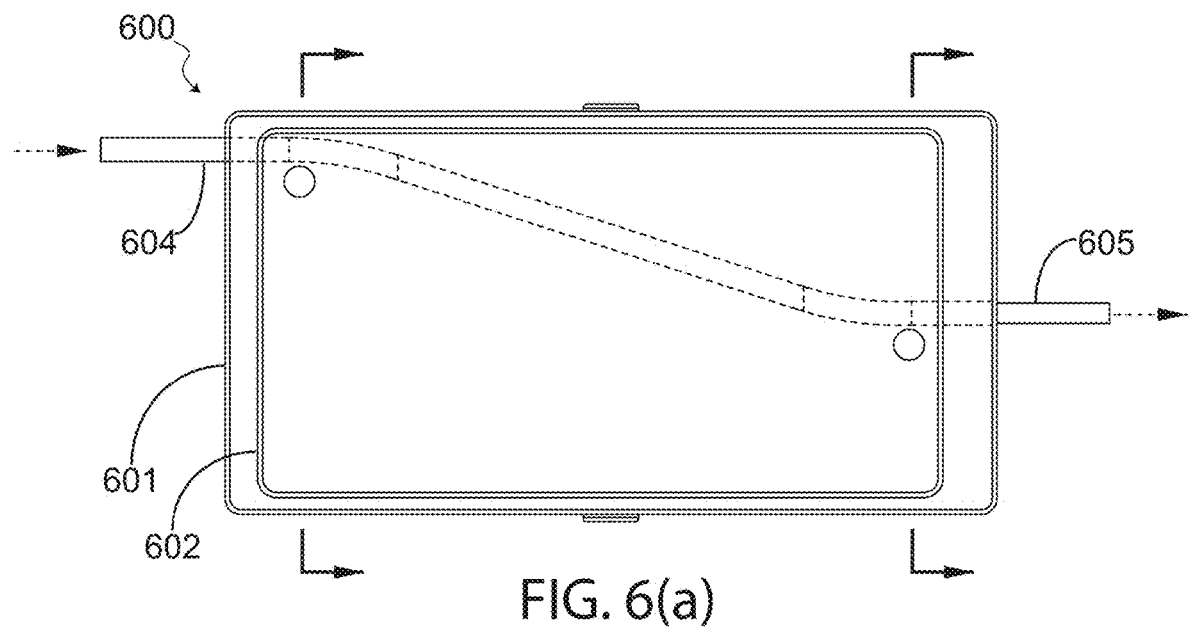
FIG. 6(a) illustrates a top cross-sectional view of a fluid warming system in accordance with an exemplary embodiment of the present invention.
Figure 6B:
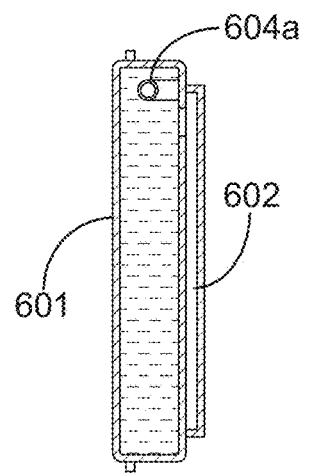
FIG. 6(b) illustrates a front view of the fluid warming system depicted in FIG. 6(a).
Figure 6C:
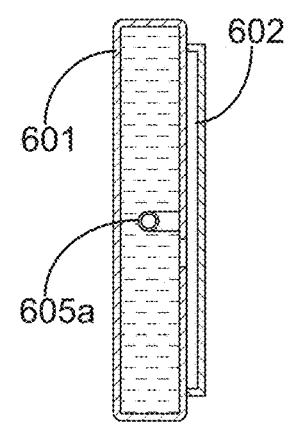
FIG. 6(c) illustrates a rear view of the fluid warming system depicted in FIG. 6(a).
Figure 6D:
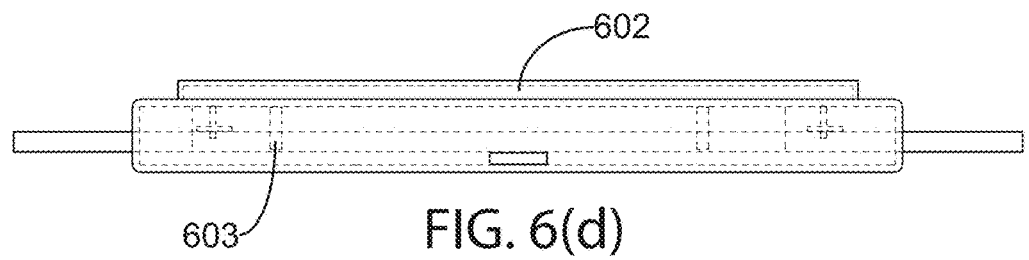
FIG. 6(d) illustrates a side cross-sectional view of the fluid warming system depicted in FIG. 6(a).

Turning now to the next figures, FIG. 5(*a*) illustrates an RF fluid warming apparatus for a system for warming fluids in accordance with an exemplary embodiment of the present invention; and FIG. 5(*b*) illustrates a cross-sectional top view of the apparatus illustrated in FIG. 5(*a*). More specifically, FIGS. 5(*a*) and 5(*b*) depict an RF fluid warming apparatus 500 that may be employed with a system similar to system 400, wherein apparatus 500 comprises: a housing including a first clam cover or shell 501; a base or shell 502, which includes a foam structure 503 comprising a pathway 504; RF choke edges 505; and clamps 506 for securing shells 501 and 502 together when closed.

Because the shells clam together and a fluid tube may be positioned along pathway 504, the present invention does not require disposable cartridges or other add-on components that may disturb a sterilized system. All that is required is any standard tubing (IV tubing, for example) which can be inserted into apparatus 500 with no breakage of the sterile closed tubing system. Of course, other structural designs may be implemented without deviating from the scope of the present invention, but FIG. 5(*a*) and FIG. 5(*b*) depict one exemplary embodiment in which a cover or clam shell 501 can mate or register with a base or shell 502 in order to form the waveguide of apparatus 500. RF chokes may be designed into mating edges 505 of each clam shell to prevent RF leakage.

Foam structure 503 may comprise a low loss foam, which as mentioned above forms a preset profile or pathway 504 for tube 504*a*. In exemplary embodiments, and in no way limiting the scope of the present invention, the foam material of foam structure 503 may be polystyrene or similar polymers. If apparatus 500 is implemented with system similar to system 400, with a separate RF source controller module (for example), input RF connectors 507 may couple the RF energy into the waveguide via a first electromagnetic port and RF connector 508 may collect any unabsorbed portion of the input power, via a second electromagnetic port, and dumps it in a matched load as explained above.

While in operation, clamps 506 for securing shell 501 and shell 502 hold the two halves of the waveguide together after the insertion or positioning of tube 504*a*; insertion or positioning of tube 504*a* may be achieved by opening the two halves and placing tube 504*a* within pathway 504 of foam structure 503 in the predefined position between inlet 509 and outlet 510. In exemplary embodiments, pathway 504 is a fitted pathway, meaning that tube 504*a* fits therein snuggly and securely. A fluid inside fluid-carrying tube 504*a* enters the waveguide at inlet 509 and leaves apparatus 500 via outlet 510. This configuration eliminates the need for a disposable cartridge that has been proposed by prior art. The advantage is twofold: (1) there is no breakage of the closed sterile infusion environment where contamination and infection can be introduced; and (2) cost of disposable cartridges proposed by prior art are entirely eliminated.

Other variations of a housing for apparatus 500 may be possible without deviating from the scope of the present invention. For example, and without limiting the present invention, shell 501 may implement a hinged means, snap on fasteners, screws, or any other fastening means. Importantly, the housing or cover should enclose the waveguide securely and in a manner that prevents leakage.

Turning now to the next set of figures, FIG. 6(*a*) illustrates a top cross-sectional view of a fluid warming system in accordance with an exemplary embodiment of the present invention, which is compact and implements a control module circuitry coupled to a compact housing configured to house a waveguide and the control module circuitry; FIG. 6(*b*) illustrates a front view of the fluid warming system depicted in FIG. 6(*a*); FIG. 6(*c*) illustrates a rear view of the fluid warming system depicted in FIG. 6(*a*); and FIG. 6(*d*) illustrates a side cross-sectional view of the fluid warming system depicted in FIG. 6(*a*). More specifically, these figures depict RF fluid warming system 600, which comprises: an RF fluid warming apparatus including a waveguide housed in a first compartment 601 of a housing with an inlet opening 604*a* and an outlet opening 605*a* for positioning a first end 604 of a fluid-carrying tube through a pathway formed within an internal structure of the waveguide; and an RF source, control module circuitry housed in a second compartment 602 adjacent to the first compartment 601, wherein the RF source and the control module circuitry comprise a printed circuit board(s) including sensors coupled therein.

This exemplary embodiment comprises a compact variation of an RF fluid warming apparatus, which offers several advantages compared to the application of standard waveguides. For example, and without deviating from the scope of the present invention, the aspect ratio of a standard waveguide may typically be 2 to 1 (i.e., in FIG. 2, $\alpha=2$ b). This is required for maximum power handling which could be as high as a megawatt of RF peak power. In an RF fluid warming apparatus in accordance with an exemplary embodiment of the present invention, the average power need not exceed 1 kW. Therefore, it is possible to reduce the waveguide height with no detrimental effect on its performance. Accordingly, the apparatus depicted in FIG. 6(*a*)-(*d*) comprises a reduced height waveguide, which reduces the size and increases the field intensity for stronger coupling to the fluid traveling through the tube.

The structure of the waveguide housed in compartment 601 is similar to that shown and described throughout this disclosure, and may include a foam structure or similar component for positioning the tube in the waveguide. However, the reduced height waveguide will be slimmer and lighter. Moreover, as shown in FIG. 6(*d*), an additional compartment is constructed on a surface to the waveguide so as to allow a printed board, or control board to be securely housed adjacent to the first compartment. The control module housed in compartment 602 typically includes, as mentioned above, the RF source and the controller circuitry. It is noted here that the RF connectors and cables are eliminated and micro-strip traces may be attached to the RF probes 603 exciting the waveguide section.

In an exemplary embodiment, the control module includes a controller configured to: manage overall control of system 600 during operation; execute failsafe operations of self-administered procedures; enable custom remote programing of warmer operating mode; and execute one or more executable instructions concerning patient-specific programing and record keeping. As may be appreciated by a person of ordinary skill in the art, other automated functions, programs and executable instructions may be implemented with system 600 without limiting or deviating from the scope of the present invention. Similarly, as with system 400, temperature sensors may be coupled to or implemented with the control module in order to implement non-invasive temperature monitoring probes at the input opening 604*a* and output opening 605*a* of the unit. As mentioned above, such feedback information may be used by the control module to adjust the output power of the RF generator and therefore, fluid temperature may be precisely controlled.

Figure 11:
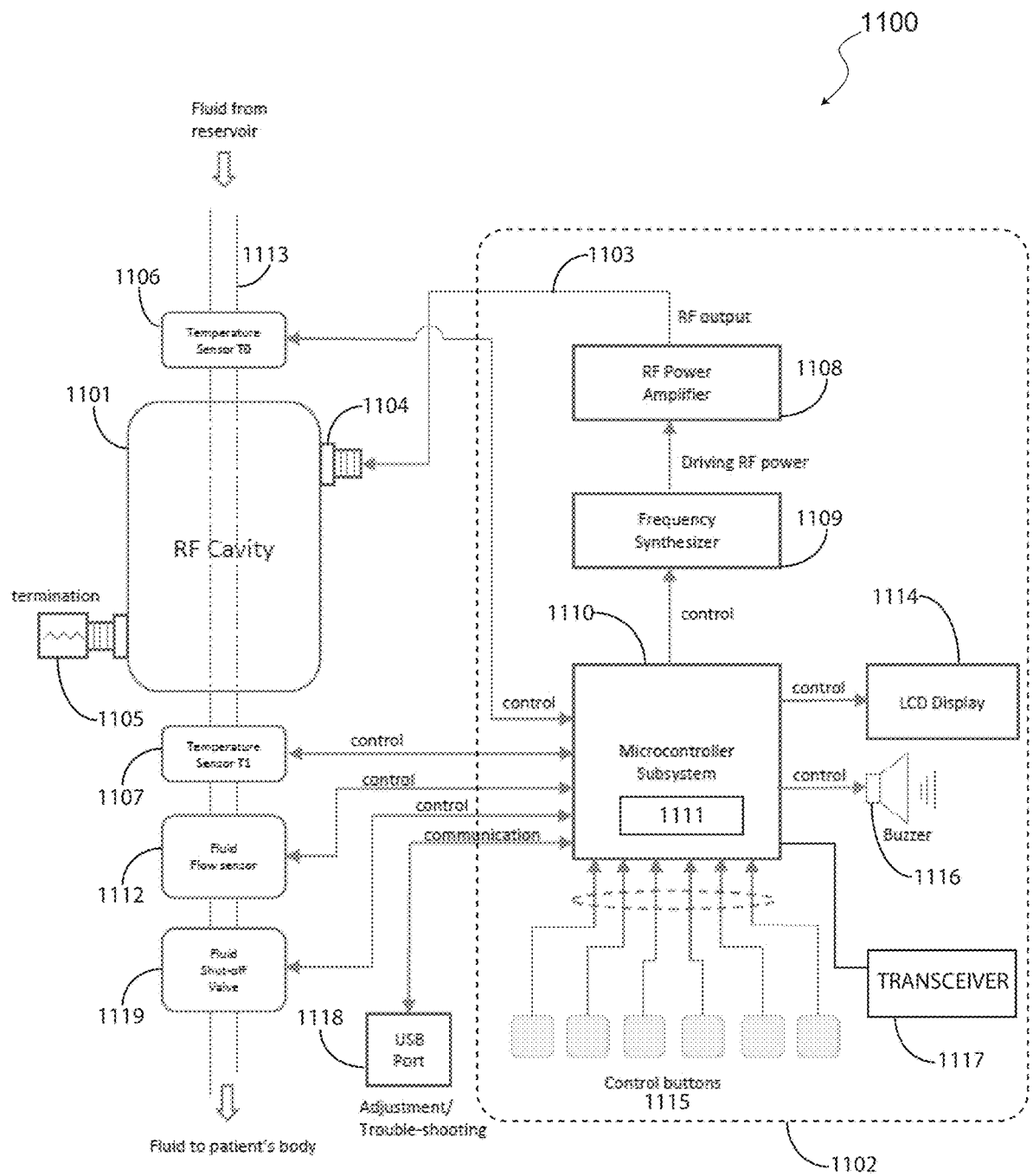
FIG. 11 illustrates a system for warming fluids in accordance with an exemplary embodiment of the present invention.

Turning now to the next set of figures, FIG. 11 illustrates a system for warming fluids in accordance with an exemplary embodiment of the present invention, and FIG. 12 illustrates a flow chart of a method for warming fluids performed by said system.

More specifically, FIG. 11 illustrates RF fluid warmer system (system 1100), which comprises: waveguide 1101; an RF source control module (control module 1102); an RF input line 1103 that introduces RF signals into waveguide 1101 via a first electromagnetic port or RF input port 1104; a termination comprising terminal port 1105 connected to an RF connector, which collects any unabsorbed portion of the input power and dumps it in a matched load; and temperature sensors 1106 and 1107 situated at an input terminal end and at an output terminal end, respectively, for non-invasively measuring (and enabling temperature monitoring and control via control module 1102) the temperature of the fluid entering and exiting waveguide 1101.

Control module 1102 may be configured to provide overall control of system 1100, and to these ends, control module 1102 may include a microcontroller 1110 with access to a memory for storing one or more sets of executable instructions for enabling different features. For example, and without limiting the scope of the present invention, one or more executable instructions may enable failsafe operation of self-administered procedures, custom remote programing of warmer operating modes, patient-specific programing, and record keeping.

Control module 1102 exemplarily includes a temperature monitoring and control system; to these ends, control module 1102 is in communication with temperature sensors 1106 and 1107 situated at an input terminal end and at an output terminal end, respectively. Moreover, control module 1102 is also in communication with RF power amplifier 1108 and frequency synthesizer 1109, for non-invasively enabling temperature monitoring and control of the temperature of the fluid entering and exiting waveguide 1101. Information received from the temperature sensors at the input and output of the waveguide may be used by microcontroller 1110 of control module 1102 to adjust an output power of RF amplifier 1108 and therefore, fluid temperature may be tightly controlled.

It is well known to experts in the field that during blood warming process care should be taken to control the maximum temperature of the blood and blood products, hence the hardware must be capable of exposing an IV liquid only to a safe level of radio frequency energy. This may be achieved by using a power control methodology such as pulse-wave-modulation (PWM). In this approach, the average RF energy is controlled by pulsing the RF power, meaning the power will be turned "On" and "Off" at a certain rate to meet the required average.

By way of example, and in no way limiting the scope of the present invention, a temperature control sub-system may comprise the following components: frequency synthesizer 1109; digital control subsystem governed by one or more executable instructions stored in a memory 1111 of microcontroller 1110; RF power amplifier 1108; one or more temperature sensors, which may comprise infra-red (IR) based temperature sensors 1106, 1107; and a flow sensor 1112.

In exemplary embodiments, the frequency synthesizer 1109 generates a 2.45 GHz single tone RF signal with Pulse Width Modulation (PWM) capability. The PWM duty-cycle is controlled by the digital control subsystem. The digital control subsystem enables the programing of the radiofrequency synthesizer circuit and other functional aspects such as outlet liquid temperature control and monitoring, and alarms.

The RF power amplifier 1108 amplifies the power intensity to the required level based on a flow rate, which is reported to the digital control subsystem via the one or more flow sensors 1112. In exemplary embodiments, this may comprise reporting a flow rate to the digital subsystem over RS485 interface or equivalent. The flow sensor 1112 is preferably non-invasive and measures the fluid low rate inside IV tube.

In exemplary embodiments, two temperature sensors (infra-red temperature sensing devices) 1106 and 1107 may be used to measure inlet and outlet IV liquid temperatures, respectively. Alternatively, radio-meter sensors may be used. These sensors are non-invasive and pick up the infra-red (or radio signals) energy stemming from the fluid flowing through tube 1113, which may be for example a typical IV tube constructed of silicone. In this manner, temperature measurement results may be read by the digital subsystem. In exemplary embodiments, this may be achieved over I2C or an equivalent alternative interface.

To facilitate user interaction, in exemplary embodiments such as the one depicted in FIG. 12, control module 1102 may include a user interface, which may include one or more devices for providing an output of information or receiving user input. For example, and without limiting the scope of the present invention, control module 1102 may include a visual output device 1114, such as an LCD display and or one or more LEDs, an input device 1115 such as one or more buttons or switches, an auditory output device 1116 such as a simple buzzer, a transceiver 1117 for communicating with external devices, such as an RS485 physical transceiver, a USB serial converter 1118, and connectors and local power supply circuits (not shown). In exemplary embodiments, memory 1111, such as a flash memory inside the microcontroller 1110, may be programmed through a dedicated connector that is also onboard.

Figure 12A:
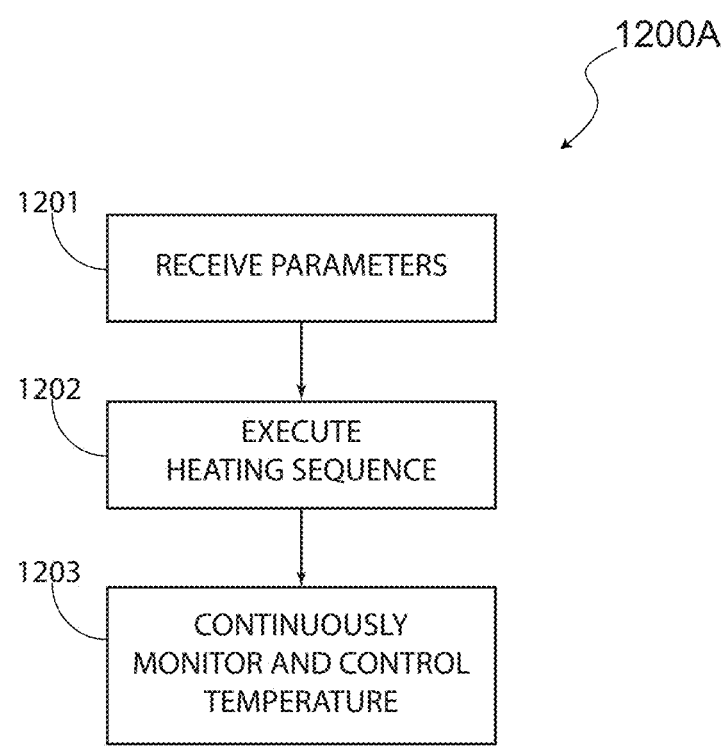
FIG. 12A illustrates a flow chart of a method for warming fluids performed by a system in accordance with an exemplary embodiment of the present invention.

Turning now to the next figure, FIG. 12A illustrates a flow chart of a method for warming fluids performed by system 1100. More specifically, FIG. 12A depicts method 1200A for warming and maintaining a desired fluid temperature performed by a radio frequency fluid warmer in accordance with the present invention.

As mentioned above, a required RF energy level may be controlled by control module 1102 based on flow rate and inlet and outlet fluid temperature. The RF energy level from the power amplifier may be controlled by means of varying its input RF duty cycle controlled by the digital subsystem. Method 1200A depicts a sequence of steps for illustrative purposes, but the sequence may include less or more steps and in alternative order, without limiting the scope of the present invention.

In step 1201, prior to the start of operation, control module 1102 (for example by way of the digital subsystem) may receive the following set of system parameters:

T_target, fluid temperature to be achieved;

$T_0$, the fluid temperature at an inlet of the RF cavity or waveguide 1101;

$T_1$, the instantaneous fluid temperature exiting at an outlet of the waveguide 1101;

$S_F$, the flow speed of the fluid; and other physical parameters of system 1100 such as length of fluid tube 1113 placed inside the waveguide 1101.

In step 1202, the system executes an initial heating sequence. This is to bring the fluid temperature $T_1$ to a value little less than the T_target, or T_target×N (%). In exemplary embodiments, the software calculates the required RF power level in order to bring the fluid temperature from $T_0$ to T_target×N (%). Based on the calculated power, the RF duty-cycle is determined and applied to the frequency synthesizer circuit. The RF power amplifier amplifies this PWM-modulated RF signal and feeds it to the RF cavity, where IV carrying fluid is flowing in the fluid tubing. During the initial heating sequence, the software waits until the $T_1$ temperature, the outlet temperature, approaches a near equilibrium point. If $T_1$ temperature is beyond the acceptable (over or under) temperature range limits of $T_1$, a fault condition is declared. When this happens, an audible alarm will sound, the flow of the fluid will shut-off, and the system will stop. This situation continues until the operator manually release and resets the fault condition. Once $T_1$ temperature reaches initial equilibrium, the heating sequence concludes.

In step 1203, upon or subsequent to a conclusion of the heating sequence the system enters a close temperature tracking phase—that is, in exemplary embodiments, the system begins to continuously monitor and control the temperature. In this step 1203, based on the difference between $T_1$ value and T_target value, the RF PWM duty-cycle may be adjusted by a small step at a time and followed by a waiting period based on system response time. The goal is to eventually reach $T_1$ within a range of a predetermined or programmed upper error limit and a predetermined or programmed lower error limit. For example, and without limiting the scope of the present invention, in exemplary embodiments, $T_1$ is monitored and controlled such that:

$T_1 \geq$ (T_target−lower error limit); and $T_1 \leq$ (T_target+upper error limit).

During this phase or step 1203, if the $T_1$ reading exceeds or drops above or below acceptable preset range, a fault condition is declared as well. Just like the initial heating phase an audible alarm will sound, the flow of fluid will stop, and the system comes to halt.

In exemplary embodiments, a user may control the operation of the system via user interface control panel that includes one or more manual, touch-screen or other means of operating control features. For example, and without limitation, simple switch or button may include "START" and "STOP" button(s) or switch(es), as well as changing vital system parameters such as T target by operating keyboards or other input means.

Figure 12B:
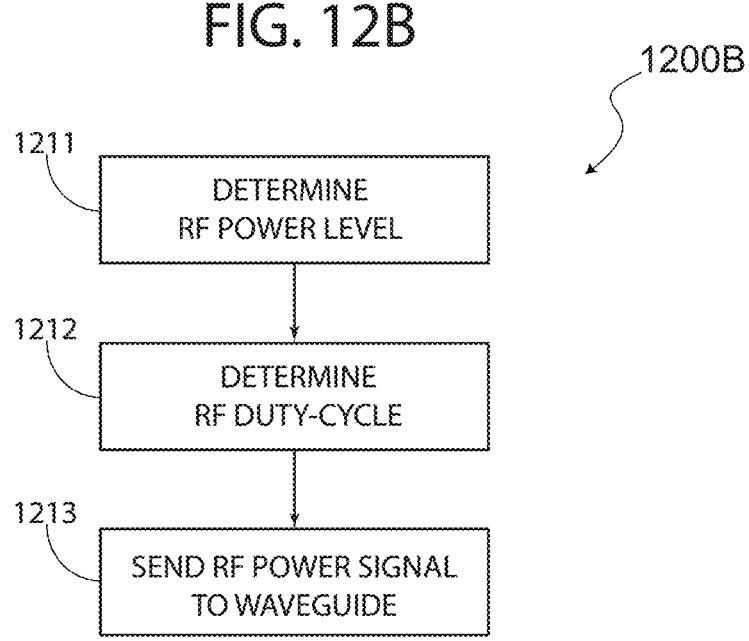
FIG. 12B illustrates a flow chart of a method for executing a heating phase performed by a control module in accordance with the present invention.

Turning now to the next figure, FIG. 12B illustrates a flow chart of a method performed by system 1100. More specifically, FIG. 12B depicts method 1200B for executing a heating phase performed by a control module in accordance with the present invention, such as control module 1102. Method 1200B depicts a sequence of steps for illustrative purposes, but the sequence may include less or more steps and in alternative order, without limiting the scope of the present invention.

In step 1211, an RF power level is determined by control module 1102, which is configured to do the same by way of one or more sets of executable instructions in memory 1111. That is, the system software calculates the required RF power level in order to bring the fluid temperature from $T_0$ to T_target×N (%) as mentioned above.

In step 1212, based on the calculated power, control module 1102 determines an RF duty-cycle and applies the determined duty-cycle to the frequency synthesizer circuit.

In step 1213, control module 1102 sends an RF power signal to the waveguide 1101. In this step, the RF power amplifier amplifies this PWM-modulated RF signal and feeds it to the RF cavity, where IV carrying fluid is flowing in the fluid tubing 1113. As mentioned above, during a heating sequence, control module 1102 waits until the $T_1$ temperature, the outlet temperature, approaches a near equilibrium point. If $T_1$ temperature is beyond the acceptable (over or under) temperature range limits of $T_1$, a fault condition is declared. When this happens, an audible alarm may sound, the flow of the fluid will shut-off, and the system will stop. This situation continues until the operator manually release and resets the fault condition. Once $T_1$ temperature reaches initial equilibrium, the heating sequence concludes and the monitoring and control phase commences, an example of which is illustrated in the following flow chart and related discussion below.

Figure 12C:
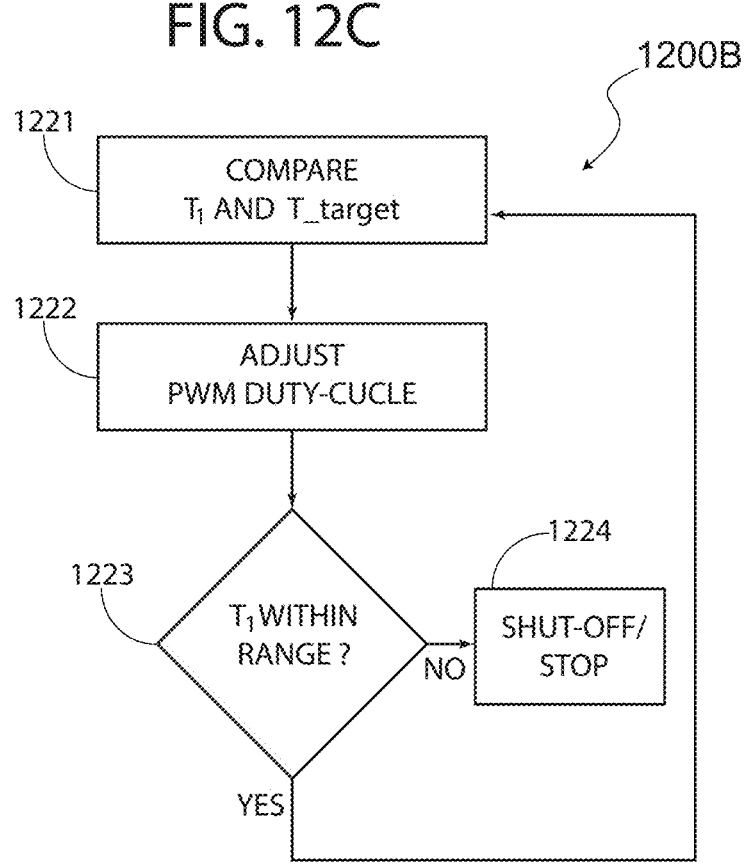
FIG. 12C illustrates a flow chart of a method for continuously monitoring and controlling a temperature of a fluid performed by a control module in accordance with the present invention.

Turning now to the next figure, FIG. 12C illustrates a flow chart of a method performed by system 1100. More specifically, FIG. 12C depicts method 1200C for continuously monitoring and controlling a temperature of a fluid performed by a control module in accordance with the present invention, such as control module 1102. Method 1200C depicts a sequence of steps for illustrative purposes, but the sequence may include less or more steps and in alternative order, without limiting the scope of the present invention.

In step 1221, control module 1102 may, by way of one or more executable instructions stored in a memory 1111 of control module 1102, continuously compare $T_1$ with T_target.

In step 1222, depending on a value difference between $T_1$ and T_target, the RF PWM duty-cycle may be adjusted by a small step at a time and followed by a waiting period based on system response time. As mentioned above, the goal is to eventually reach $T_1$ within a range of a predetermined or programmed upper error limit and a predetermined or programmed lower error limit, such that, for example, $T_1 \geq$ (T_target−lower error limit), and $T_1 \leq$ (T_target+upper error limit).

In step 1223, control module 1102 may check that $T_1$ is maintained within an acceptable range. In the event that $T_1$ is not within an acceptable range, as mentioned above, control module 1102 may, in step 1224, shut off. This step may further include setting off an audible alarm will. Moreover, this step may include actuating shut-off valve 1119 in order to stop the flow of fluid and bringing system 1100 to halt.

Figure 12D:
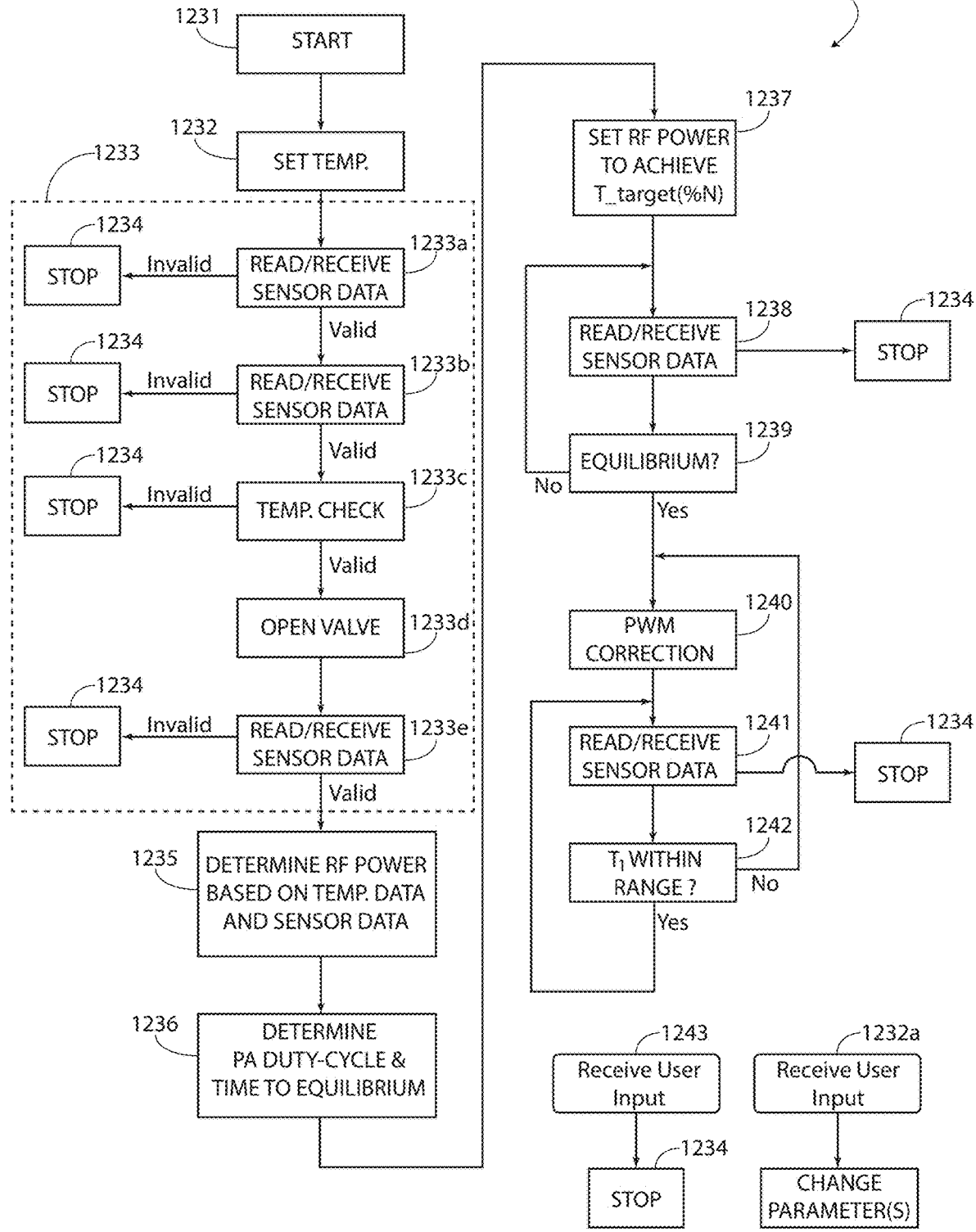
FIG. 12D illustrates a flow chart of a method for warming fluids performed by a system in accordance with an exemplary embodiment of the present invention.

Turning now to the next figure, FIG. 12D illustrates a flow chart of a method for warming fluids performed by control module 1102. It is understood that although method 1200C is depicted with a particular sequence of steps, such is for illustrative purposes, and the sequence may include less or more steps and in alternative order(s), without limiting the scope of the present invention.

In step 1231, system 1100 may be started. This may include supplying power to control module 1102, switching an "ON" button of control module 1102, or any other user-initiated input instructing control module 1102 to begin a routine or otherwise star a method of warming fluids introduced into waveguide 1101 of system 1100.

In step 1232, a target temperature may be set. That is, a target temperature (T_target) may be provided to control module 1102. In some exemplary embodiments, T_target is provided via executable instructions such as a program or routine stored in memory 1111 of microcontroller 1110. In some exemplary embodiments, T_target is provided via executable instructions such as a program or routine stored in an external memory such as an external device that may be coupled to control module 1102. For example, a USB device may be used to provide instructions, including a T_target via USB port 1118. In some exemplary embodiments, T_target is provided via a user interface configured to receive user inputs such as entry into an alphanumeric keypad, a numeric keypad, touchscreen device, one or more dials, buttons or switches, and the like. As such, whether entered manually or by other means, a target temperature may be set at this step 1232.

Other parameters that may be similarly provided to control module 1102 in step 1232. In exemplary embodiments, such parameters may include, but are not limited to: T_target, fluid temperature to be achieved; To, the fluid temperature at an inlet of the RF cavity or waveguide 1101; $T_1$, the instantaneous fluid temperature exiting at an outlet of the waveguide 1101; $S_F$, the flow speed of the fluid; and any other physical parameters of system 1100 such as length of fluid tube 1113 placed inside the waveguide 1101.

In step 1233, a system check sequence may be performed. For example, and by way of illustration and without limiting the scope of the present invention, a series of steps 1233a-1234 may be performed in order to ensure system 1100 is performing or will perform adequately. As part of the system check of step 1233, an initial sensor data read may be performed at step 1233a, by which data is received from a first temperature sensor 1106, typically situated at an inlet region of waveguide 1101 so that a reading of temperature at the inlet is received by control module 1102.

Accordingly, in step 1233a, control module 1102 may compare the sensor data from sensor 1106 to a stored initial temperature range for sensor 1106 to test that a valid $T_0$ will be read when operation starts and a fluid flows inside tube 1113 and is passed through a pathway of waveguide 1101. In case of a reading outside of a predetermined acceptable range for sensor 1106, i.e., an invalid reading, a shut-off sequence may be executed at step 1234, whereby control module 1102 shuts off power, sets off an alarm via an audible output 1116, provides a message via a visual output device 1114, or otherwise stops operation. In exemplary embodiments, a valid reading of sensor data at step 1233a, will result in a second sensor reading in step 1233b.

In step 1233b, control module 1102 may compare the sensor data from sensor 1107 to a stored initial temperature range for sensor 1107 to test that a valid $T_1$ will be read when operation starts and a fluid flows inside tube 1113 and is passed through a pathway of waveguide 1101 and eventually exits via an outlet of the waveguide 1101. In case of a reading outside of a predetermined acceptable range for sensor 1107, i.e., an invalid reading, a shut-off sequence may be executed at step 1234, whereby control module 1102 shuts off power, sets off an alarm via an audible output 1116, provides a message via a visual output device 1114, or otherwise stops operation. In exemplary embodiments, a valid reading of sensor data at step 1233b, will result in a temperature check in step 1233c.

In step 1233c, a temperature check is performed to make sure that an equilibrium, between the temperature of the fluid traveling inside tube 1113 at an inlet of waveguide 1101 and the temperature of the fluid traveling inside tube 1113 at an outlet of waveguide 1101, may be maintained by system 1100. In case of a reading outside of a predetermined acceptable range or difference between sensor 1106 and sensor 1107, i.e., an invalid reading, a shut-off sequence may be executed at step 1234, whereby control module 1102 shuts off power, sets off an alarm via an audible output 1116, provides a message via a visual output device 1114, or otherwise stops operation. In exemplary embodiments, a valid reading of the temperature check at step 1233c, will result in opening a valve so that a fluid within tube 1113 can enter the waveguide 1101 in step 1233d.

In step 1233d, control module 1102 may activate or actuate valve 1119 in order to allow a fluid to begin flowing through fluid tube 1113.

In step 1233d, a fluid flow check is performed. In tis step, control module 1102 may compare the sensor data from sensor 1119 to a stored fluid flow sensor range for sensor 1119 to test that a valid $S_F$, the flow speed of the fluid, can be continuously read during operation. In case of a reading outside of a predetermined acceptable range for sensor 1119, i.e., an invalid reading, a shut-off sequence may be executed at step 1234, whereby control module 1102 shuts off power, sets off an alarm via an audible output 1116, provides a message via a visual output device 1114, or otherwise stops operation. In exemplary embodiments, a valid reading of fluid flow sensor 1119 at step 1233d, will result in a successful conclusion of the system check or sequence 1233, and control module 1102 may initiate a set of necessary calculations or determinations to begin warming IV fluids at step 1235.

In step 1235, control module 1102 may determine a necessary RF power based on readings from a predetermined or provided T_target, the fluid temperature to be achieved, To, the fluid temperature at the inlet of the RF cavity or waveguide 1101, $T_1$, the instantaneous fluid temperature exiting at the outlet of the waveguide 1101, $S_F$, the flow speed of the fluid passing through waveguide 1101, and other physical parameters of system 1100 such as length of fluid tube 1113 placed inside the waveguide 1101, etc.

In step 1236, control module 1102 may determine a PA duty-cycle and a time to equilibrium in order to continuously monitor and control a temperature of the fluid.

In step 1237, control module 1102 may set power amplifier 1108 and configure the PWM duty-cycle achieve N (%) of the target temperature.

In steps 1238-1239, control module 1102 may read or receive data from sensor 1107 and compare that temperature data to data from sensor 1106. If an equilibrium is reached or reached within an acceptable range, then a PWM correction may be adjusted at step 1240. Alternatively, if the readings or difference between that data of sensor 1107 and sensor 1106 are not within an acceptable range such that an acceptable temperature equilibrium has not been conserved between an inlet and outlet of waveguide 1101, then a shut-off sequence as mentioned above in step 1234 may be executed.

In steps 1241, data may be read or received from sensor 1107. If the readings is not within an acceptable range or limit, then a shut-off sequence as mentioned above in step 1234 may be executed for safety precautions.

In step 1242, control module 1102 may compare the temperature data from sensor 1107 to the T_target value. If the temperature reading from sensor 1107 is not within an acceptable range of the T_target value, then the RF PWM duty-cycle may be adjusted at step 1240 by a small step at a time and followed by a waiting period based on system response time. As mentioned above, the goal in these series of steps 1241-1242 is to eventually reach $T_1$ within a range of a predetermined or programmed upper error limit and a predetermined or programmed lower error limit such that $T_1$ is monitored and controlled in order to achieve a temperature whereby $T_1 \geq (\text{T\_target} - \text{lower error limit})$ and $T_1 \leq (\text{T\_target} + \text{upper error limit})$. This cycle continues as fluid continues to flow through waveguide 1101 and thus the temperature continuously monitored and controlled.

In exemplary embodiments, at any point or predetermined phase of the fluid warming and temperature monitoring process, parameters may be selectively changed. To these ends, at step 1232a, a user may provide control module 1102 inputs via a user interface of control module 1102, or by way of a device that may be coupled to or in communication with control module 1102. Similarly, vie the same input means, a user may provide control module 1102 inputs via a user interface of control module 1102 to stop or suspend operation thereof.

A typical application of the apparatus discussed here would be warming of peritoneal dialysis dialysate prior to infusion. However, peritoneal dialysis is used here as just one example of how this device can be used as a warmer of biological, pharmaceutical or otherwise medical fluids. Other applications may include administration of blood during warfare or armed combat, in which soldiers require quick transfusions due to sever battle wounds. A system in accordance with the present invention is typically compact and highly portable, which means a waveguide a control module may be compact enough to take on the field by armed forces or medical personnel, carried by first responders in emergency vehicles, or easily transported with a patient—whether at a hospital, clinic or at the patient's home.

An apparatus for warming fluids using radio frequency has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A method performed by radio frequency fluid warmer system, comprising the steps of:
   controlling a power level of a radio frequency generator coupled to a first electromagnetic port of a waveguide, wherein the waveguide includes a resistive termination coupled to a second electromagnetic port of the waveguide for preserving a matched waveguide condition, and wherein the waveguide is adapted to receive a fluid-carrying tube positioned between an inlet and an outlet of the waveguide;
   receiving sensing data from one or more sensors situated in proximity to the inlet or the outlet of the waveguide; and
   monitoring a parameter of a fluid inside the fluid-carrying tube based on sensing data from the one or more sensors.

2. The method of claim 1, wherein controlling the power level of the radio frequency generator, comprises:

adjusting the power level of the radio frequency generator based on the sensing data from the one or more sensors.

3. The method of claim 1, wherein controlling the power level of the radio frequency generator, comprises:
adjusting the power level of the radio frequency generator to bring a fluid temperature at the inlet of the waveguide ($T_0$) to a value less than a target temperature (T_target×N (%)).

4. The method of claim 1, wherein controlling the power level of the radio frequency generator, comprises:
adjusting the power level of the radio frequency generator to bring a fluid temperature at the inlet of the waveguide ($T_0$) to at least a near equilibrium with a fluid temperature at the outlet of the waveguide ($T_1$).

5. The method of claim 1, further comprising:
adjusting a pulse-wave-modulation (PWM) duty-cycle based on the sensing data of the one or more sensors.

6. The method of claim 1, further comprising:
determining a waiting period based on a system response time.

7. The method of claim 1, wherein controlling the power level of the radio frequency generator, comprises:
adjusting the power level of the radio frequency generator to bring a fluid temperature at the outlet of the waveguide ($T_1$) within a temperature range of a programmable upper error limit (T_target+upper error limit) and a programmable lower error limit T_target−lower error limit such that:
$T_1 \geq$ (T_target−lower error limit); and
$T_1 \leq$ (T_target+upper error limit).

8. The method of claim 1, further comprising:
triggering a shut-off sequence in response to determining a fault condition based on the sensing data of the one or more sensors.

9. The method of claim 8, wherein the shut-off sequence includes one or more of:
shutting off a fluid flow by activating a valve in fluid communication with the fluid-carrying tube;
shutting off a power supply to the radio frequency generator;
activating an audible indicator; or
activating a visual indicator.

10. The method of claim 1, wherein the one or more parameters include:
a fluid temperature at the inlet of the waveguide;
a fluid temperature at the outlet of the waveguide; or
a flow speed of the fluid inside the fluid-carrying tube.

* * * * *